United States Patent
Mori et al.

(10) Patent No.: US 7,834,190 B2
(45) Date of Patent: Nov. 16, 2010

(54) PROCESS FOR PRODUCTION OF OPTICALLY ACTIVE-3-AMINO-2-HYDROXYPROPIONIC CYCLOPROPYLAMIDE DERIVATIVES AND SALTS THEREOF

(75) Inventors: Kohei Mori, Takasago (JP); Akira Nishiyama, Takasago (JP); Naoaki Taoka, Takasago (JP); Daisuke Moriyama, Takasago (JP); Nobuo Nagashima, Takasago (JP)

(73) Assignee: Kaneka Corporation, Osaka (JP)

( * ) Notice: Subject to any disclaimer, the term of this patent is extended or adjusted under 35 U.S.C. 154(b) by 111 days.

(21) Appl. No.: 12/227,788

(22) PCT Filed: May 22, 2007

(86) PCT No.: PCT/JP2007/060435

§ 371 (c)(1),
(2), (4) Date: Nov. 26, 2008

(87) PCT Pub. No.: WO2007/138928

PCT Pub. Date: Dec. 6, 2007

(65) Prior Publication Data

US 2010/0048909 A1 Feb. 25, 2010

(30) Foreign Application Priority Data

May 26, 2006 (JP) ............... 2006-146745

(51) Int. Cl.
*C07D 263/08* (2006.01)
*C07D 303/02* (2006.01)
(52) U.S. Cl. .................... 548/237; 549/513
(58) Field of Classification Search ........... 548/237; 549/513
See application file for complete search history.

(56) References Cited

U.S. PATENT DOCUMENTS

| | | | |
|---|---|---|---|
| 6,218,156 | B1 | 4/2001 | Yasohara et al. |
| 6,448,052 | B2 | 9/2002 | Yasohara et al. |
| 7,220,564 | B2 | 5/2007 | Kizaki et al. |
| 2005/0137139 | A1 | 6/2005 | Perni et al. |
| 2005/0153900 | A1 | 7/2005 | Velazquez et al. |
| 2005/0197301 | A1 | 9/2005 | Njoroge et al. |
| 2007/0178565 | A1 | 8/2007 | Kizaki et al. |
| 2007/0225297 | A1* | 9/2007 | Perni et al. ............. 514/255.05 |
| 2008/0305534 | A1 | 12/2008 | Moriyama et al. |

FOREIGN PATENT DOCUMENTS

| | | |
|---|---|---|
| WO | 98/35025 | 8/1998 |
| WO | 2004/027055 | 4/2004 |
| WO | 2005/035525 | 4/2005 |
| WO | 2005/058821 | 6/2005 |
| WO | 2005/123921 | 12/2005 |

OTHER PUBLICATIONS

International Search Report dated Aug. 7, 2007 in the International (PCT) Application PCT/JP2007/060435 of which the present application is the U.S. National Stage.
Shu-Hui Chen et al., "P1 and P1' Optimization of [3,4]-Bicycloproline P2 Incorporated Tetrapeptidyl α-Ketoamide Based HCV Protease Inhibitors", Letters in Drug Design & Discovery, vol. 2, pp. 118-123, 2005.
Brent D. Feske et al., "Chemoenzymatic formal total synthesis of (-)-bestatin", Tetrahedron: Asymmetry, vol. 16, pp. 3124-3127, 2005.
Yun Gao et al., "Catalytic Asymmetric Epoxidation and Kinetic Resolution: Modified Procedures Including in Situ Derivatization", J. Am. Chem. Soc., vol. 109, pp. 5765-5780, 1987.
Akio Fujii et al., "Ruthenium(II)-Catalyzed Asymmetric Transfer Hydrogenation of Ketones Using a Formic Acid—Triethylamine Mixture", J. Am. Chem. Soc., 118, pp. 2521-2522, 1996.
Manuel Pastor et al., "A Strategy for the Incorporation of Water Molecules Present in a Ligand Binding Site into a Three-Dimensional Quantitative Structure—Activity Relationship Analysis", J. Med. Chem., vol. 40, No. 25, pp. 4089-4102, 1997.
J. Augusto R. Rodrigues et al, "A highly enantioselective chemoenzymatic synthesis of *syn*-3-amino-2-hydroxy esters: key intermediates for taxol side chain and phenylnorstatine", Tetrahedron: Asymmetry, vol. 16, No. 18, pp. 3099-3106, 2005.
Takashi Ohshima et al., "Catalytic asymmetric epoxidation of α, β-unsaturated carboxylic acid imidazolides and amides by lanthanide—BINOL complexes", Tetrahedron, vol. 59, No. 52, pp. 10485-10497, 2003.
Beena Bhatia et al., "A Cobalt Catalyzed Protocol for the Synthesis of Substituted β-Phenyl Isoserine Derivatives", Tetrahedron Letters, vol. 37, No. 40, pp. 7311-7314, 1996.
Form PCT/IB/338 together with International Preliminary Report on Patentability and translation of PCT Written Opinion mailed Dec. 24, 2008 for International (PCT) Application No. PCT/JP2007/060435 of which the present application is the U.S. National Stage.

* cited by examiner

*Primary Examiner*—Kamal A Saeed
*Assistant Examiner*—Samantha L Shterengarts
(74) *Attorney, Agent, or Firm*—Wenderoth, Lind & Ponack, L.L.P.

(57) ABSTRACT

An objective of the present application is to provide an industrially practicable method for producing an optically-active 3-amino-2-hydroxypropionic cyclopropylamide derivative or salt thereof from an inexpensive easily-available starting material. The derivative or salt thereof is useful as an intermediate for a medicine. It is also intended by the present application to provide a useful intermediate of the derivative. The objective is attained by the following method. First, an easily-available 2-halo-3-oxopropionic acid derivative is asymmetrically reduced, and then epoxidated to produce an optically-active epoxycarboxylic acid derivative. Next, the derivative is converted into an optically-active epoxyamide derivative by reaction with cyclopropylamine, and then reacted with a nitrile to obtain an optically-active oxazolinamide derivative. Subsequently, selective acid solvolysis of the oxazoline skeleton gives the optically-active 3-amino-2-hydroxypropionic cyclopropylamide derivative or salt thereof.

18 Claims, No Drawings

PROCESS FOR PRODUCTION OF OPTICALLY ACTIVE-3-AMINO-2-HYDROXYPROPIONIC CYCLOPROPYLAMIDE DERIVATIVES AND SALTS THEREOF

TECHNICAL FIELD

The present invention relates to a process for producing an optically-active 3-amino-2-hydroxypropionic cyclopropylamide derivative and salt thereof useful as an intermediate for a medicine, and to an intermediate useful for the production thereof.

BACKGROUND ART

As the method for producing an optically-active 3-amino-2-hydroxypropionic cyclopropylamide derivative and salt thereof, the following examples are known.

(1) A method for producing 3-amino-2-hydroxy-hexanoic cyclopropylamide hydrochloride, wherein L-N-(tert-butoxycarbonyl)-norvaline is reacted with N,O-dimethylhydroxyamine in the presence of a condensing agent to obtain Weinreb amide; the amide is reduced into an aldehyde; cyclopropylisonitrile is added thereto to give (2S,3S)-3-N-tert-butoxycarbonylamino-2-acetoxyhexanoic cyclopropylamide; then the acetyl group and the tert-butoxycarbonyl group are cleavaged (Patent Reference 1, Patent Reference 2).

(2) A method for producing (2S,3S)-3-amino-2-hydroxyhexanoic cyclopropylamide, wherein hydrocyanic acid is added to an aldehyde derived from L-N-(tert-butoxycarbonyl)-norvaline; then the tert-butoxycarbonyl group is cleavaged and the cyano group is hydrolyzed to give 3-amino-2-hydroxy-hexanoic acid; the nitrogen is protected with benzyloxycarbonyl group; then the protected acid is condensed with cyclopropylamine using a condensing agent and is hydrogenolyzed (Patent Reference 3, Non-Patent Reference 1).

However, the method (1) could not be said to be a realistic method, since expensive L-N-(tert-butoxycarbonyl)-norvaline is used as the starting material, expensive and dangerous lithiumaluminium hydride is used in the reduction step, and a hardly-available isonitrile derivative is used in the step of carbon increase for the aldehyde.

Also, the method (2) is not economical and is difficult to be industrially carried out and could not be said to be an efficient synthetic method, since an expensive L-N-(tert-butoxycarbonyl)-norvaline derivative is used as the starting material, a deadly poisonous hydrocyanic acid is used, and the number of the process steps are increased because of the repetition of protection and deprotection on the nitrogen atom.

Consequently, all of the production methods for an optically-active 3-amino-2-hydroxypropionic cyclopropylamide derivative and salt thereof known at present have a serious problem in point of the economical aspect, and are not practicable from the viewpoint of industrial practicability.

Patent Reference 1: WO2005/058821
Patent Reference 2: US2005/0197301
Patent Reference 3: WO2005/035525
Non-Patent Reference 1: Letters in Drug Design & Discovery, 2005, 118-123

DISCLOSURE OF THE INVENTION

Problems that the Invention is to Solve

In consideration of the above, an objective of the present invention is to provide a practicable method for industrial production, capable of readily producing an optically-active 3-amino-2-hydroxypropionic cyclopropylamide derivative and salt thereof useful as an intermediate for a medicine, from an inexpensive and easily-available starting material; and to provide an intermediate useful for production of the optically-active 3-amino-2-hydroxypropionic cyclopropylamide derivatives and salt thereof.

Means for Solving the Problems

As a result of assiduous studies in consideration of the above, the present inventors achieved a development of a method capable of readily producing a 3-amino-2-hydroxypropionic cyclopropylamide derivative and salt thereof useful as an intermediate for a medicine, from an inexpensive and easily-available starting material.

Specifically, the present invention relates to an optically-active oxazolinamide derivative represented by the following formula (1):

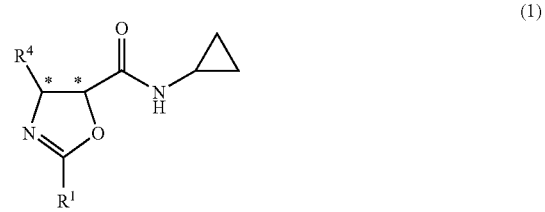

wherein, * indicates an asymmetric carbon atom; $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent.

The present invention also relates to an optically-active epoxyamide derivative represented by the following formula (3):

wherein, * and $R^4$ are the same as above.

The present invention also relates to an optically-active oxazoline carboxylic acid derivative represented by the following formula (5):

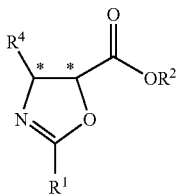
(5)

wherein, *, $R^1$ and $R^4$ are the same as above; $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent.

The present invention also relates to an optically-active epoxycarboxylic acid salt represented by the following formula (13):

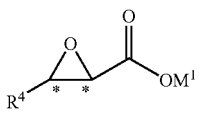
(13)

wherein, * and $R^4$ are the same as above; $M^1$ represents an alkali metal.

The present invention also relates to a compound represented by the following formula (17):

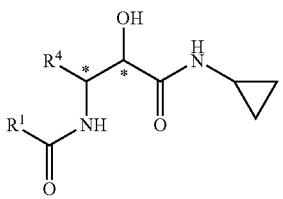
(17)

wherein, *, $R^1$ and $R^4$ are the same as above.

The present invention also relates to a method for producing an optically-active 2-halo-3-hydroxypropionic acid derivative; comprising a step of asymmetric reduction of a 2-halo-3-oxopropionic acid derivative represented by the following formula (10):

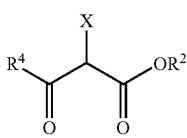
(10)

wherein, $R^2$ and $R^4$ are the same as above; X represents a halogen atom;

wherein the optically-active 2-halo-3-hydroxypropionic acid derivative is represented by the following formula (11):

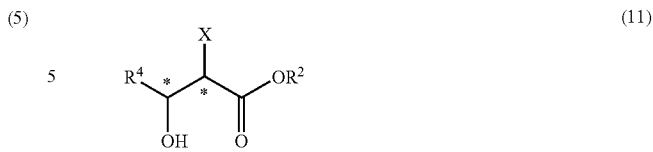
(11)

wherein, *, $R^2$, $R^4$ and X are the same as above.

The present invention also relates to a method for producing an optically-active epoxyamide derivative represented by the formula (3); comprising a step of reacting an optically-active epoxycarboxylic acid derivative represented by the following formula (7):

(7)

wherein, *, $R^2$ and $R^4$ are the same as above; with a cyclopropylamine represented by the following formula (6):

(6)

The present invention also relates to a method for producing an optically-active oxazolinamide derivative; comprising a step of reacting an optically-active epoxyamide derivative represented by the formula (3) with a nitrile represented by the following formula (4):

$R^1CN$ (4)

wherein, $R^1$ is the same as above in a presence of an acid catalyst;

wherein the optically-active oxazolinamide derivative is represented by the following formula (1):

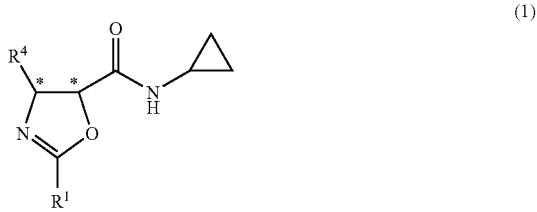
(1)

wherein, *, $R^2$ and $R^4$ are the same as above.

The present invention also relates to a method for producing an optically-active oxazolinamide derivative represented by the formula (1); comprising steps of reacting an optically-active epoxycarboxylic acid derivative represented by the formula (7) with a nitrile represented by the formula (4) in a presence of an acid catalyst to produce an optically-active oxazolinecarboxylic acid derivative represented by the formula (5); and then reacting the optically-active oxazolinecarboxylic acid derivative with a cyclopropylamine represented by the formula (6).

The present invention also relates to a method for producing an optically-active 3-amino-2-hydroxypropionic cyclopropylamide derivative or salt thereof; comprising a step of selective acid hydrolysis or acid alcoholysis of an oxazoline ring of an optically-active oxazolinamide derivative represented by the formula (1);

wherein the optically-active 3-amino-2-hydroxypropionic cyclopropylamide derivative is represented by the following formula (2):

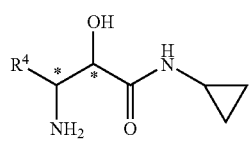

(2)

wherein, * and $R^4$ are the same as above.

The present invention also relates to a method for producing an optically-active 3-amino-2-hydroxypropionic cyclopropylamide derivative or salt thereof represented by the formula (2); comprising steps in the order of (i) acid hydrolysis of an optically-active oxazolinecarboxylic acid derivative represented by the formula (5); (ii) protecting a 3-position amino group; (iii) condensation with a cyclopropylamine represented by the formula (6):

(iv) deprotection, in that order; or comprising steps in the order of (i) alkali-hydrolysis of the compound of the formula (5); (ii) condensation with the cyclopropylamine of the formula (6); and (iii) hydrolysis of a 3-position amide group.

BEST MODE FOR CARRYING OUT THE INVENTION

The present invention relates to all the steps shown in the following scheme:

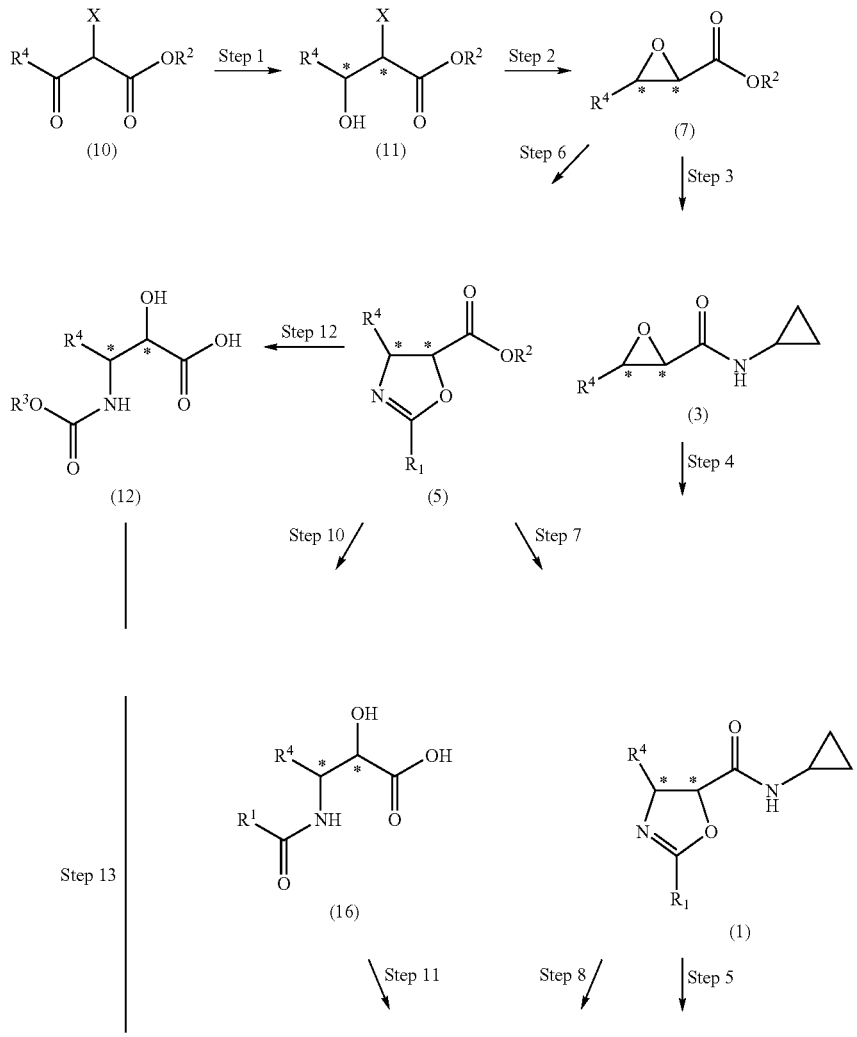

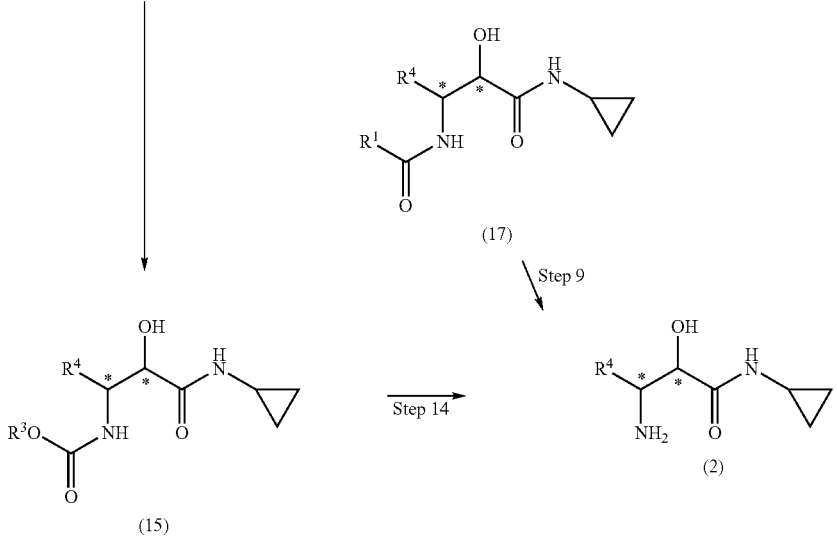

For obtaining the compound represented by the formula (2) in the present invention, any compound shown in the above scheme can be a starting compound. It may be suitably determined depending on the starting compound what step should be carried out.

In the following, the each step in the present invention is described in order.

Step 1

In the step, a 2-halo-3-oxopropionic acid derivative represented by the following formula (10):

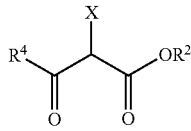

is asymmetrically reduced to produce an optically-active 2-halo-3-hydroxypropionic acid derivative represented by the following formula (11):

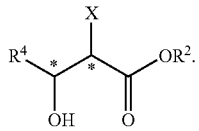

The 2-halo-3-oxopropionic acid derivative as a starting material can be readily produced by halogenating a commercially-available 3-oxopropionic acid derivative with a halogenating agent such as thionyl chloride, sulfuryl chloride, bromine and phosphorus tribromide. For example, sulfuryl chloride may be used according to the method described in Tetrahedron Asymmetry, 16 (2005), 3124-3127.

In the above, * indicates an asymmetric carbon atom. $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent. The substituent includes, for example, a halogen atom such as a fluorine atom, a chlorine atom, a bromine atom and an iodine atom; a nitro group. The number of the substituent may be 0 to 3. $R^2$ is preferably a hydrogen atom, a methyl group, an ethyl group, an n-propyl group, an isopropyl group, an n-butyl group, a vinyl group, an allyl group, a phenyl group or a benzyl group. More preferably, $R^2$ is a hydrogen atom, a methyl group or an ethyl group. X represents a halogen atom, preferably a chlorine atom or a bromine atom, more preferably a chlorine atom.

$R^4$ represents an alkyl group having 1 to 20 carbon atoms and optionally having a substituent, or an aralkyl group having 7 to 20 carbon atoms and optionally having a substituent. The substituent includes, for example, a halogen atom such as a fluorine atom, a chlorine atom, a bromine atom and an iodine atom; a nitro group, an amino group, a hydroxyl group or a thiol group. The number of the substituent may be 0 to 3. $R^4$ is preferably an n-propyl group, a cyclobutylmethyl group or a benzyl group, more preferably an n-propyl group.

A method of asymmetric reduction in the step is not specifically limited as long as the method is capable of stereoselectively reducing a carbonyl group of the compound (10). The method includes [1] a method of reduction using a hydride reducing agent modified with an optically-active compound, [2] a method of hydrogenation in a presence of an asymmetric transition metal catalyst, [3] a method of hydrogen transfer reduction in a presence of an asymmetric metal catalyst or [4] a method of reduction with a microorganism or an enzyme derived from a microorganism.

In the method [1], a hydride reducing agent modified with an optically-active compound specifically includes a reducing agent prepared from optically-active tartaric acid and sodium borohydride, a reducing agent prepared from an optically-active oxaborolysine derivative and borane, a reducing agent prepared from an optically-active ketoiminato-type cobalt complex and sodium borohydride and tetrahydrofuran-2-methanol, a reducing agent prepared from optically-active 1,1'-bi-2-naphthol and lithiumaluminium hydride.

An amount of a hydride reducing agent modified with an optically-active compound to be used may be 5 molar times or less, more preferably 0.5 to 2 molar times, relative to the compound (10).

A reaction solvent includes ether solvents such as tetrahydrofuran, 1,4-dioxane and ethylene glycol dimethyl ether; hydrocarbon solvents such as benzene, toluene and hexane; and halogen-containing solvents such as methylene chloride and chloroform. One of them may be singly used, or two or more may be used in combination. Preferred are ether solvents such as tetrahydrofuran and ethylene glycol dimethyl ether. When a mixed solvent is used, a blend ratio is not specifically limited.

A reaction temperature is preferably −100 to 60° C., more preferably from −78 to 20° C., from a viewpoint of shortening a reaction time, increasing a selectivity in reduction and increasing a production yield.

In the reaction, a method of adding the compound (10), an asymmetric reducing agent and a solvent, and an order of addition thereof are not specifically limited.

Any ordinary treatment for collecting a product from a reaction mixture may be carried out as a treatment after the reaction. For example, a target compound can be obtained by removing a transition metal catalyst from a reaction mixture after the reaction through filtration under reduced pressure or under pressure and then evaporating away a reaction solvent through an operation of reduced pressure heating or the like. The obtained compound has a sufficient purity enough for use in the subsequent step; however, a purity of the compound may be further increased by an ordinary purification method such as crystallization, fractional distillation and column chromatography for a purpose of further increasing a yield in the subsequent step or increasing a purity of the compound to be obtained in the subsequent step.

In the case of hydrogenation in a presence of an asymmetric transition metal catalyst (above-mentioned method [2]), a metal complex with an element of Group VIII of the Periodic Table, such as ruthenium, rhodium, iridium and platinum, is preferable; and ruthenium complex is more preferable from a viewpoint of a stability and easy availability of the complex and an economical aspect, as a transition metal catalyst. A phosphine ligand is preferable as an asymmetric ligand in the metal complex, and a bidentate ligand is preferable as a phosphine ligand. As the bidentate ligand, preferred are BINAP: 2,2'-bisdiphenylphosphino-1,1'-binaphthyl; BINAP derivatives such as Tol-BINAP: 2,2'-bis(di-p-tolylphosphino-1,1'-binaphthyl; BDPP: 2,4-bis(diphenylphosphino)pentane; DIOP: 4,5-bis(diphenylphosphinomethyl)-2,2-dimethyl-1,3-dioxane; BPPFA: 1-[1',2-bis(diphenylphosphino)ferrocenyl] ethylamine; CHIRAPHOS: 2,3-bis(diphenylphosphino)butane; DEGPHOS: 1-substituted-3,4-bis(diphenylphosphino) pyrrolidine; DuPHOS: 1,2-bis(2,5-substituted phosphorano) benzene; DIPAMP: 1,2-bis[(o-methoxyphenyl) pheylphosphino]ethane, or the like; and more preferred is BINAP: 2,2'-bisdiphenylphosphino-1,1'-binaphthyl. As the BINAP complex, (BINAP)RuBr$_2$, (BINAP)RuCl$_2$, [(BINAP)RuCl$_2$]NEt$_3$ and the like are preferable.

An amount of an asymmetric transition metal catalyst to be used is preferably 0.2 molar times or less, and more preferably 0.05 to 0.0001 molar times, relative to the compound (10).

A hydrogen pressure in the step is preferably 1 to 100 kg/cm$^2$, more preferably 1 to 30 kg/cm$^2$.

A reaction solvent includes water; alcohol solvents such as methanol, ethanol and isopropanol; ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen-containing solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; phosphonic triamide solvents such as hexamethylphosphonic triamide. One of them may be singly used, or two or more may be used in combination. Preferred are water and alcohol solvents such as methanol, ethanol and isopropanol; and more preferred is a mixed solvent of such an alcohol solvent and water. Even more preferred is a mixed solvent of methanol and water.

When a mixed solvent of an alcohol solvent and water is used, a blend ratio of alcohol solvent/water may be arbitrarily determined; but the ratio by volume of alcohol solvent/water is preferably 100/1 to 1/1, more preferably 20/1 to 4/1.

An amount of a solvent to be used is preferably 50 times by weight or less, more preferably 5 to 20 times by weight, relative to the compound (10).

A reaction temperature is preferably −20 to 100° C., more preferably 0 to 70° C., from a viewpoint of shortening a reaction time, increasing a selectivity in reduction and increasing a production yield.

In the reaction, a method of adding the compound (10), an asymmetric reducing agent and a solvent, and an order of addition thereof are not specifically limited.

An ordinary treatment for obtaining a product from a reaction mixture may be carried out as a treatment after the reaction. For example, a target compound can be obtained by removing a transition metal catalyst from a reaction mixture after the reaction through filtration under reduced pressure or under pressure and then evaporating away a reaction solvent through an operation of reduced pressure heating or the like. The obtained compound has a sufficient purity enough for use in the subsequent step; however, a purity of the compound may be further increased by an ordinary purification method such as crystallization, fractional distillation and column chromatography for a purpose of further increasing a yield in the subsequent step or increasing a purity of the compound to be obtained in the subsequent step.

In the case of hydrogen transfer reduction in a presence of an asymmetric transition metal catalyst (above-mentioned method [3]), a hydrogen-donating compound may be specifically used in a presence of an optically-active diamine catalyst represented by the following formula (24):

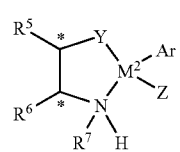

(24)

In the catalyst (24), * indicates an asymmetric carbon atom. $M^2$ represents a transition metal such as palladium, rhodium, ruthenium, iridium, platinum, zirconium, titanium, chromium, cobalt, copper, nickel, zinc, manganese, iron, ytterbium, lanthanum and samarium. Among them, ruthenium, rhodium and iridium are preferable.

$R^5$ and $R^6$ may be the same or different; and represents an alkyl group having 1 to 20 carbon atoms and optionally having a substituent, an aryl group having 6 to 20 carbon atoms and optionally having a substituent, or an aralkyl group having 7 to 20 carbon atoms and optionally having a substituent; and a combination of $R^5$ and $R^6$ may form a ring.

The alkyl group having 1 to 20 carbon atoms and optionally having a substituent includes, for example, a methyl group, an ethyl group, a propyl group, an isopropyl group, a tert-butyl group, a cyclopentyl group and a cyclohexyl group. The aryl group having 6 to 20 carbon atoms and optionally having a substituent includes, for example, a phenyl group, a p-methoxyphenyl group, a p-chlorophenyl group, a p-nitrophenyl group, a p-methylphenyl group and a naphthyl group. The aralkyl group having 7 to 20 carbon atoms and optionally having a substituent includes, for example, a benzyl group. A combination of $R^5$ and $R^6$ forming a ring together includes, for example, a tetramethylene group. From a viewpoint of a stereoselectivity in reaction, preferable $R^5$ and $R^6$ is a phenyl group or a tetramethylene group.

$R^7$ represents a hydrogen atom, an alkyl group having 1 to 20 carbon atoms and optionally having a substituent, an aralkyl group having 7 to 20 carbon atoms and optionally having a substituent, or an aryl group having 6 to 20 carbon atoms and optionally having a substituent. A specific example may be the same described above. From a viewpoint of a yield and a stereoselectivity, a hydrogen atom or a methyl group is preferable, and a hydrogen atom is more preferable.

Ar represents an optionally-substituted aromatic compound; and includes, for example, benzene, toluene, xylene, mesitylene, hexamethylbenzene, ethylbenzene, tert-butylbenzene, p-cymene, cumene or pentamethylcyclopentadienyl. Among them, benzene, mesitylene or p-cymene is preferable.

Z represents a halogen atom, an alkylsulfonyloxy group optionally having a substituent, an arylsulfonyloxy group optionally having a substituent or an aralkylsulfonyloxy group optionally having a substituent; and includes, for example, a fluorine atom, a chlorine atom, a bromine atom, an iodine atom, a trifluoromethanesulfonyloxy group, a methanesulfonyloxy group or a p-toluenesulfonyloxy group. Among them, a chlorine atom or a trifluoromethanesulfonyloxy group is preferable.

Y represents an oxygen atom, an alkylsulfonylamide group having 1 to 20 carbon atoms and optionally having a substituent, an arylsulfonylamide group having 6 to 20 carbon atoms and optionally having a substituent, or an aralkylsulofnylamide group having 7 to 20 carbon atoms and optionally having a substituent. The alkylsulfonylamide group having 1 to 20 carbon atoms and optionally having a substituent includes, for example, a methanesulfonylamide group, a trifluoromethanesulfonylamide group or a camphorsulfonylamide group.

The arylsulfonylamide group having 6 to 20 carbon atoms and optionally having a substituent includes, for example, a benzenesulfonylamide group, a p-toluenesulfonylamide group, a mesitylenesulfonylamide group, a p-trifluoromethylbenzenesulfonylamide group, a 1-naphthalenesulfonylamide group or a 2-naphthalenesulfonylamide group. The aralkylsulofnylamide group having 7 to 20 carbon atoms and optionally having a substituent includes, for example, a benzylsulfonylamide group. Among them, preferred is a p-toluenesulfonylamide group, a camphorsulfonylamide group, a mesitylenesulfonylamide group, a 1-naphthalenesulfonylamide group or a 2-naphthalenesulfonylamide group, from the viewpoint of the yield and the stereoselectivity.

The catalyst (24) specifically includes, for example, RuCl[(R,R)—NpDPEN](p-cymene) complex, RuCl[(S,S)—NpDPEN](p-cymene) complex, RuOTf[(R,R)—NpDPEN](p-cymene) complex or RuOTf[(S,S)—NpDPEN](p-cymene) complex. (S,S)—NpDPEN means (1S,2S)—N-mono(1-naphthalenesulfonyl)-1,2-diphenylethylenediamine; OTf means trifluoromethanesulfonyloxy group. For example, RuCl[(R,R)—NpDPEN](p-cymene) complex is represented by the following formula (25):

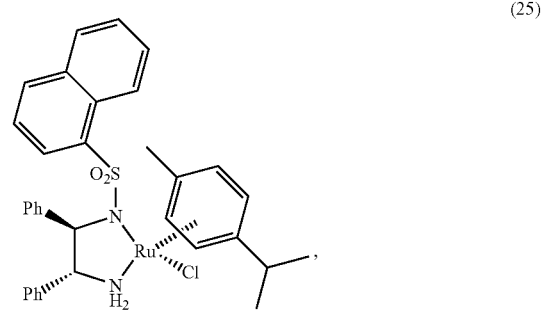

(25)

RuOTf[(R,R)—NpDPEN](p-cymene) complex is represented by the following formula (26):

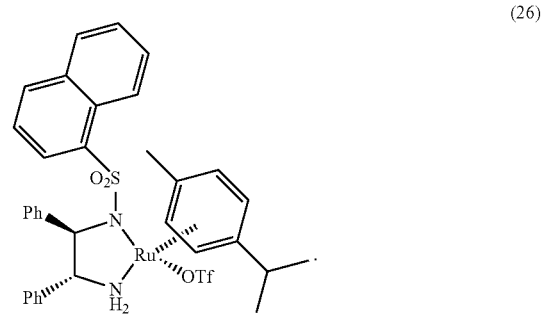

(26)

The catalyst (24) to be used in the step may be synthesized according to a method described in J. Am. Chem. Soc., 1996, 118, 2521, or may be a commercial product. The catalyst (24) for use in the step may be previously prepared, and isolated and purified; or may be prepared in a reaction mixture and may be directly used as it is.

An amount of the catalyst (24) to be used in the step is not specifically limited; but may be generally 0.00001 to 1 molar time, preferably 0.0001 to 0.2 molar times, relative to an optically-active 2-halo-3-hydroxypropionic acid derivative represented by the formula (10).

A hydrogen-donating compound to be used in the step is not specifically limited; but includes, for example, alcohols such as methanol, ethanol, n-propanol and isopropanol; formic acid; formates such as sodium formate and ammonium formate. Especially, formic acid or sodium formate is preferable, and formic acid is more preferable, from a viewpoint of a yield.

An amount of a hydrogen-donating compound to be used in the step is not specifically limited; but may be generally 1 to 100 molar times, preferably 1 to 10 molar times, relative to an optically-active 2-halo-3-hydroxypropionic acid derivative represented by the formula (10).

A base may be further added for the purpose of promoting the reaction of the step. The base includes, for example, inorganic bases such as sodium hydroxide, potassium hydroxide and potassium carbonate; metal alkoxides such as sodium methoxide and potassium tert-butoxide; and amines such as triethylamine, trimethylamine and ammonia. In case where formic acid is used as a hydrogen-donating compound, it is preferable to further add the base, especially the amine such as triethylamine, trimethylamine and ammonia.

When a base is used in the step, an amount thereof to be used is not specifically limited. In general, the amount may be 0.01 to 100 molar times, preferably 0.1 to 10 molar times, more preferably 1 to 10 molar times, relative to an optically-active 2-halo-3-hydroxypropionic acid derivative of the formula (10).

When a hydrogen-donating compound to be used in the step is liquid or a base to be further added is liquid, a reaction solvent is not specifically needed. Solvent-free reaction may be preferable in point that the reaction can be completed within a short period of time and an amount of a catalyst to be used may be reduced; however, in case where a solubility of a reaction substrate is low, a reaction solvent may be further used.

A reaction solvent is not specifically limited as long as the solvent does not interfere with the reaction; however includes, for example, the hydrocarbon solvents; ester solvents; nitrile solvents; ether solvents; amide solvents; sulfoxide solvents; halogen-containing solvents; alcohol solvents; carboxylic acid solvents such as formic acid and acetic acid; water. One of them may be singly used, or two or more may be used in combination. When a mixed solvent is used, a blend ratio is not specifically limited.

A concentration of an optically-active 2-halo-3-hydroxypropionic acid derivative represented by the formula (10) in the reaction varies, depending on a reaction solvent to be used; but may be generally 1 to 90% by weight, preferably 4 to 30% by weight.

A reaction temperature in the step varies, depending on a type and an amount of an optically-active transition metal complex and a hydrogen-donating compound to be used, and a kind of a reaction solvent; but may be generally within a range of from a solidification point to a boiling point of the reaction solvent used. For a purpose of completing the reaction within a short period of time, the reaction temperature is preferably kept high; but the reaction temperature is preferably kept low from a viewpoint of suppressing a side reaction. In general, the temperature may be −20 to 150° C., preferably 0 to 70° C.

A reaction time varies, depending on a kind and an amount of an optically-active diamine catalyst and a hydrogen-donating compound to be used, a kind of a reaction solvent and a reaction temperature. When the reaction temperature is 0 to 70° C., the time is generally 1 to 36 hours.

An order of adding an optically-active 2-halo-3-hydroxypropionic acid derivative represented by the formula (10), an optically-active diamine represented by the formula (24), a hydrogen-donating compound, a base, a reaction solvent and others may be any desired one, and is not specifically limited. Preferably, a hydrogen-donating compound is added to a mixture of an optically-active 2-halo-3-hydroxypropionic acid derivative represented by the formula (10) and an optically-active diamine represented by the formula (24). When a base is added, it is also desirable that a hydrogen-donating compound is added to a mixture of an optically-active 2-halo-3-hydroxypropionic acid derivative represented by the formula (10) and an optically-active diamine represented by the formula (24). A hydrogen-donating compound may be added all at a time, or may be continuously or intermittently added during the reaction. In case where a vapor is generated with a progress of the reaction, it is preferable from a point of safety to successively add the compound along with a progress of the reaction.

Any ordinary treatment for collecting a product from a reaction mixture may be carried out as a treatment after the reaction. For example, a target compound can be obtained by removing a transition metal catalyst from a reaction mixture after the reaction through filtration under reduced pressure or under pressure and then evaporating away a reaction solvent through an operation of reduced pressure heating or the like. The obtained compound has a sufficient purity enough for use in the subsequent step; however, a purity of the compound may be further increased by an ordinary purification method such as crystallization, fractional distillation and column chromatography for a purpose of further increasing a yield in the subsequent step or increasing a purity of the compound to be obtained in the subsequent step.

In the case of reduction with a microorganism or a microorganism-derived enzyme (above-mentioned method [4]), preferred is a method of reduction with an enzyme derived from a microorganism for industrial practice. Hereinunder described is a method of producing the compound (11) by stereoselective reduction of the compound (10) in a presence of a source of enzyme having an ability to stereoselectively reduce a carbonyl group of the compound (10).

An "enzyme source" includes not only an enzyme itself having a reducing activity but also a culture and a processed product of a microorganism having a reducing activity. The "culture of microorganism" means a culture containing microorganismic cells, or cultured cells, or may also be a processed product thereof. The "processed product" means, for example, a crude extract, a freeze-dried cell product, an acetone-processed cell product, a pulverized product of those cells, or the like. The enzyme source may be fixed in any known method to be a fixed enzyme or fixed cell product for use herein. The fixation may be carried out in any method known to those skilled in the art, such as a crosslinking method, a physical adsorption method and clathration method.

In the present invention, an enzyme source having an ability to (2S,3S)-selectively reduce a carbonyl group of the compound (10) includes enzyme sources derived from microorganisms belonging to a genus *Candida, Debaryomyces, Kluyveromyces, Metschnikowia, Pichia, Saccharomycopsis, Williopsis, Achromobacter, Arthrobacter, Acidiphilium, Cellulomonas, Devosia, Microbacterium, Micrococcus, Ochrobactrum, Oerskovia, Pseudomonas, Paenibacillus, Streptomyces, Saccharopolyspora, Aegerita* or *Crinipellis.*

Preferred are enzyme sources derived from microorganisms such as *Candida etchellsii, Candida guilliermondii, Candida lactis-condensi, Candida oleophila, Candida solani, Candida fermentati, Debaryomyces carsonii, Debaryomyces robertisiae, Debaryomyces castellii, Debaryomyces polymorphus, Kluyveromyces thermotolerans, Metschnikowia bicuspidata* var. *bicuspidata, Pichia bovis, Pichia anomala, Pichia haplophila, Saccharomycopsis malanga, Williopsis saturnus* var. *suaveolens, Achromobacter xylosoxidans* subsp. *denitrificans, Arthrobacter crystallopoietes, Arthrobacter nicotianae, Arthrobacter protophormiae, Acidiphilium cryptum, Cellulomonas* sp., *Cellulomonas fermentans, Devosia riboflavina, Microbacterium arborescens, Micrococcus luteus, Ochrobactrum* sp., *Oerskovia turbata, Pseudomonas stutzeri, Pseudomonas putida, Paenibacillus alvei, Streptomyces aureus, Streptomyces cacaoi* subsp. *asoensis, Streptomyces coelescens, Streptomyces griseoaurantiacus, Streptomyces hydrogenans, Streptomyces salmonis, Saccharopolyspora erythraea, Aegerita candida, Crinipellis stipitaria,* and the like.

An enzyme source having an ability to (2R,3R)-selectively reduce a carbonyl group of the compound (10) includes enzyme sources derived from microorganisms belonging to a genus *Ambrosiozyma, Brettanomyces, Candida, Cryptococcus, Debaryomyces, Hanseniaspora, Issatchenkia, Kluyveromyces, Kuraishia, Ogataea, Pachysolen, Pichia, Saccharomycodes, Saccharomycopsis, Schizosaccharomyces, Saturnispora, Torulaspora, Williopsis, Zygosaccharomyces, Corynebacterium, Cladosporium, Cordyceps, Coriolus, Dendryphiella, Emericella, Fusarium, Gloeophyllum, Lentinula, Macrophoma, Monascus, Myrothecium, Nannizzia, Panus, Penicillium, Plectosphaerella, Pycnoporus, Phanerochaete, Scopulariopsis, Umbelopsis* or *Verticillium.*

Preferred are enzyme sources derived from microorganisms such as *Ambrosiozyma philentoma, Brettanomyces custersianus, Candida cantarellii, Candida haemulonii, Candida pini, Candida maris, Candida pararugosa, Candida stellata, Candida zeylanoides, Cryptococcus terreus, Debaryomyces nepalensis, Hanseniaspora valbyensis, Issatchenkia terricola, Kluyveromyces lactis* var. *drosophilarum, Kluyveromyces lactis* var. *lactis, Kuraishia capsulata, Ogataea glucozyma, Pachysolen tannophilus, Pichia angusta, Pichia holstii, Pichia jadinii, Pichia pastoris, Pichia petersonii, Pichia rhodanensis, Pichia wickerhamii, Pichia membranifaciens, Pichia xylosa, Rhodotorula minuta, Saccharomyces unisporus, Saccharomyces bavanus, Saccharomyces cerevisiae hansen, Saccharomyces cerevisiae* var. *ellipsoideus, Saccharomyces uvarum, Saccharomyces pastorianus, Saccharomycodes ludwigii, Saccharomycopsis crataegensis, Saccharomycopsis javanensis, Schizosaccharomyces pombe, Saturnispora dispora, Torulaspora globosa, Williopsis saturnus* var. *saturnus, Zygosaccharomyces bailii, Zygosaccharomyces rouxii, Corynebacterium flavescens, Corynebacterium glutamicum, Cladosporium resinae, Cordyceps subsessilis, Coriolus consors, Dendryphiella salina, Emericella nidulans* var. *nidulans, Emericella unguis, Fusarium anguioides, Gloeophyllum trabeum, Lentinula edodes, Macrophoma commelinae, Monascus purpureus, Myrothecium verrucaria, Nannizzia gypsea* var. *incurvata, Panus lacomtei, Penicillium janthinellum, Plectosphaerella cucumerina, Pycnoporus coccineus, Phanerochaete chrysosporium, Rhizopus niveus, Rhisopus oryzae, Rhizopus stolonifer* var. *stolonifer, Scopulariopsis brevicaulis, Sporotrichum aurantiacum, Umbelopsis vinacea, Verticillium niveostrastosum,* and the like.

A microorganism to derive a reducing enzyme may be any of wild strain or mutant strain. Further, also usable is microorganism induced according to a genetic method of cell fusion, gene manipulation or the like. In addition, a recombinant microorganism having the ability to produce a microorganism-derived reducing enzyme is also usable. The recombinant microorganism capable of producing the enzyme may be obtained, for example, by a method containing a step of isolating and/or purifying the enzyme to determine a part or all of an amino acid sequence of the enzyme; a step of preparing a DNA sequence coding for the enzyme, based on the amino acid sequence; a step of introducing the DNA to a different microorganism to obtain a recombinant microorganism; and a step of cultivating the recombinant microorganism to obtain the enzyme (refer to WO98/35025).

Such a recombinant microorganism includes a microorganism transformed with a vector having a DNA coding a reducing enzyme. As a host microorganism, *Escherichia coli* is preferable. More preferred is a culture of *Escherichia coli* transformed with a glycerol dehydrogenase derived from *Cellulomonas* sp.; specifically *Escherichia coli* HB101(pTSCS) of which deposition number is FERM BP-10024 (deposited in the National Institute of Advanced Industrial Science and Technology, International Patent Organism Depository, Tsukuba Center No. 6, 1-1-1, Higashi, Tsukuba-shi, Ibaragi-ken, on May 12, 2004) transformed with a vector having a glycerol dehydrogenase gene derived from *Cellulomonas* sp. KNK0102 strain (refer to WO2005/123921), and *Escherichia coli* HB101(pNTDR) of which a deposition number FERM BP-08457 (deposited in the National Institute of Advanced Industrial Science and Technology, International Patent Organism Depository, Tsukuba Center No. 6, 1-1-1, Higashi, Tsukuba-shi, Ibaragi-ken, on May 29, 2002) transformed with a vector having a carbonyl reductase gene derived from *Devosia riboflavina* NBRC13584 strain (see WO2004/027055), and the like.

A culture medium for a microorganism to be used for an enzyme source is not specifically limited as long as the culture medium may be any one in which the microorganism can grow. For example, usable is an ordinary liquid medium containing saccharides such as glucose and sucrose, alcohols such as ethanol and glycerol, fatty acids and esters thereof such as oleic acid and stearic acid, oils such as rapeseed oil and soybean oil, as a carbon source; ammonium sulfate, sodium nitrate, peptone, casamino acid, corn steep liquor, wheat bran, yeast extract and the like, as a nitrogen source; magnesium sulfate, sodium chloride, calcium carbonate, potassium monohydrogenphosphate, potassium dihydrogenphosphate and the like, as inorganic salts; and malt extract, meat extract and the like, as other nutrient sources. A cultivation may be aerobically carried out, and in general, a cultivation time may be 1 to 5 days or so, a pH of the medium may be 3 to 9, and a cultivation temperature may be 10 to 50° C.

In the present invention, a reduction of a carbonyl group of the compound (10) may be carried out by adding the compound (10) to be a substrate, a coenzyme NAD(P)H and a culture of a microorganism or a processed product thereof or the like, to a suitable solvent, and by stirring the mixture under pH control.

A reaction condition varies depending on an enzyme, microorganism or processed product thereof to be used, a substrate concentration and others; but in general, a substrate concentration may be about 0.1 to 100% by weight, preferably 1 to 60% by weight; an amount of a coenzyme NAD(P)H may be 0.000001 to 1 molar time, preferably 0.00001 to 0.001 molar times, relative to the substrate; a reaction temperature may be 10 to 60° C., preferably 20 to 50° C.; a reaction pH may be 4 to 9, preferably 5 to 8; and a reaction time may be 1 to 120 hours, preferably 1 to 72 hours.

An organic solvent may be mixed in a reaction mixture. The organic solvent includes, for example, toluene, ethyl acetate, n-butyl acetate, hexane, isopropanol, methanol, diisopropyl ether, acetone, dimethyl sulfoxide. A substrate may be added all at a time or continuously.

A reaction may be carried out batchwise or continuously.

In a reduction step in the present invention, an ordinary coenzyme NAD(P)H regeneration system may be used in combination, whereby an amount of an expensive coenzyme to be used may be significantly reduced. As a typical NAD(P)H regeneration system, for example, there is a method of using a glucose dehydrogenase and glucose.

When a similar reaction as above is carried out, using a culture or a processed product thereof or the like of a transformed microorganism prepared by introducing a reductase gene and a gene of an enzyme having an ability to regenerate a coenzyme on which a reductase depends (e.g., glucose dehydrogenase) into the same host microorganism, or that is, a transformed microorganism prepared by introducing a DNA coding the reductase of the present invention and a gene of an enzyme having an ability to regenerate a coenzyme on which the reductase depends (e.g., glucose dehydrogenase)

into the same host microorganism, it is unnecessary to separately prepare an enzyme source necessary for regeneration of the coenzyme; and therefore the compound (11) can be produced more inexpensively.

Such a transformed microorganism includes a microorganism transformed with a plasmid having both DNA coding a reductase and a DNA coding an enzyme having an ability to regenerate a coenzyme on which the reductase depends. The enzyme having the ability to regenerate the coenzyme is preferably a glucose dehydrogenase, more preferably a glucose dehydrogenase derived from *Bacillus megaterium*. The host microorganism is preferably *Escherichia coli*. Such a preferable transformed microorganisms includes *Escherichia coli* HB101(pTSCSG1) (refer to WO2005/123921), and *Escherichia coli* HB101(pNTRDG1) of which deposition number is FERM BP-08458 (deposited in the National Institute of Advanced Industrial Science and Technology, International Patent Organism Depository, Tsukuba Center No. 6, 1-1-1, Higashi, Tsukuba-shi, Ibaragi-ken, on May 29, 2002).

A transformed microorganism may be cultivated in any ordinary liquid nutrient medium containing a carbon source, a nitrogen source, an inorganic salt, an organic nutrient and others, so far as the microorganism can grow therein. An activity of an enzyme having a coenzyme-regenerating capability in the transformed microorganism can be determined according to an ordinary method. For example, regarding an activity of glucose dehydrogenase, 100 mM of glucose, 2 mM of a coenzyme NADP or NAD and the enzyme are added to 1 M of a tris-hydrochloride buffer (pH 8.0), and a reaction is carried out at 25° C. for 1 minute, and the activity may be calculated from an absorbance at a wavelength of 340 nm of the reaction mixture.

In case where a reduction step in the present invention is carried out in combination with a coenzyme regeneration system or by a use of a culture of a transformed microorganism or a processed product thereof as an enzyme source, a more inexpensive oxidized NAP(P) may be added as a coenzyme to attain the reaction.

The compound (11) produced as a result of a reduction can be purified according to an ordinary method. For example, a reaction mixture is processed for centrifugation, filtration or the like to remove suspended substances of cells and others, and then extracted using an ordinary extraction solvent such as ethyl acetate, diethyl ether, methylene chloride, toluene, hexane, and the like. A reaction solvent and an extraction solvent are evaporated away from the obtained extract through operation of heating under reduced pressure or the like, to obtain an intended product. The thus-obtained product may have a sufficient purity enough for use in the subsequent step; however, a purity of the product may be further increased by an ordinary purification method of crystallization, fractional distillation, column chromatography or the like for a purpose of further increasing a yield in the subsequent step or increasing a purity of the compound to be obtained in the subsequent step.

Step 2

In the step, an optically-active 2-halo-3-hydroxypropionic acid derivative represented by the formula (11) is reacted with a base to produce an optically-active epoxycarboxylic acid derivative represented by the following formula (7):

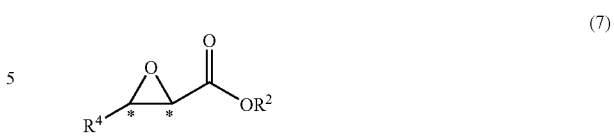

In the above, *, $R^2$ and $R^4$ are the same as above. The compound (11) may be one produced in the step 1, or may be obtained separately.

Such a base is not specifically limited; but includes tertiary amines such as triethylamine, tri-n-butylamine, N-methylmorpholine, N-methylpiperidine, diisopropylethylamine, pyridine, N,N-dimethylaminopyridine and 1,4-diazabicyclo[2,2,2]octane; metal hydroxides such as lithium hydroxide, sodium hydroxide, potassium hydroxide, barium hydroxide and magnesium hydroxide; metal carbonates such as lithium carbonate, sodium carbonate and potassium carbonate; metal hydrogencarbonates such as lithium hydrogencarbonate, sodium hydrogencarbonate and potassium hydrogencarbonate; metal alkoxides such as lithium methoxide, lithium ethoxide, sodium methoxide, sodium ethoxide, potassium methoxide, potassium ethoxide and potassium tert-butoxide. Preferred are 1,4-diazabicyclo[2,2,2]octane, lithium hydroxide, sodium hydroxide, potassium hydroxide, lithium carbonate, sodium carbonate, potassium carbonate, sodium methoxide, sodium ethoxide, potassium methoxide and potassium ethoxide; and more preferred are sodium carbonate, potassium carbonate, sodium methoxide, sodium ethoxide, potassium methoxide and potassium ethoxide.

An amount of a base to be used is preferably 0.5 to 10 molar times, more preferably from 0.5 to 5 molar times, relative to the compound (11).

A reaction solvent includes water; alcohol solvents such as methanol, ethanol and isopropanol; ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile, propionitrile and benzonitrile; halogen-containing solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; phosphonic triamide solvents such as hexamethylphosphonic triamide. One of them may be singly used, or two or more may be used in combination. Preferred are water; alcohol solvents such as methanol, ethanol and isopropanol; nitrile solvents such as acetonitrile, propionitrile and benzonitrile.

An amount of a solvent to be used is preferably 50 times by weight or less, more preferably 20 times by weight or less, relative to the compound (11).

An addition method and an addition order of the compound (11), a base and a reaction solvent in the reaction are not specifically limited.

A treatment after the reaction may be any ordinary treatment for collecting a product from a reaction mixture. For example, a reaction mixture after the reaction is neutralized by adding water and optionally an aqueous acid solution such as an aqueous hydrochloric acid solution and an aqueous sulfuric acid solution thereto; and then is extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, to obtain an intended product. The thus-obtained product may have a sufficient purity enough for use in the subsequent step; however, a purity of the product may be further increased by an ordinary purification method of crystallization, fractional distillation, column chromatography or the like for a purpose of further increasing a yield in the subsequent step or increasing a purity of the compound to be obtained in the subsequent step.

Regarding a stereochemistry of the compound (7) obtained in the step, when a tertiary amine, a metal carbonate or a metal hydroxide is used as a base, a diastereomer ratio of the compound (11) is reflected almost directly as such onto a diastereomer ratio of the product of the compound (7). Specifically, the (2S,3R) compound (7) is obtained from the (2R,3R) compound (11), and the (2R,3R) compound (7) is obtained from the (2S,3R) compound (11). The (2R,3S) compound (7) is obtained from the (2S,3S) compound (11), and the (2S,3S) compound (7) is obtained from the (2R,3S) compound (11).

On the other hand, when a metal alkoxide is used as a base, the reaction goes on along with 2-position epimerization. As a result, a trans form of the compound (7) is obtained at high selectivity, not depending on a diastereomer ratio of the starting compound (11). Specifically, the (2S,3R) compound (7) is obtained from the (2R,3R) compound (11) and (2S,3R) compound (11), and the (2R,3S) compound (7) is obtained from the (2S,3S) compound (11) and (2R,3S) compound (11).

Regarding a stereochemistry thereof, the compound (7) is preferably (2S,3R) or (2R,3S).

Step 3

In the step, an optically-active epoxycarboxylic acid derivative represented by the formula (7) is reacted with cyclopropylamine represented by the following formula (6):

(6)

thereby producing an optically-active epoxyamide derivative represented by the following formula (3):

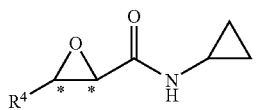

(3)

In the above, * and $R^4$ are the same as above.

The compound (3) obtained in the step is a novel compound not described in literatures, which is useful as an intermediate for a medicine.

A method for obtaining the compound (7) is not specifically limited. For example, according to a method described in U.S. Pat. No. 5,773,629, the compound (7) having a racemic form is synthesized through Darzens reaction of an aldehyde and a chloroacetate, and then processed for optical resolution with a microorganism-derived enzyme such as lipase to obtain an optically-active form of the compound (7); or according to a method described in J. Am. Chem. Soc., 1987, 109, 5765, an allyl alcohol derivative is asymmetrically epoxidated, and then a hydroxyl group is oxidized to obtain the compound (7) having an optically-active form. Preferably, the compound produced according to the step 2 is used.

In the step,

[1] the compound (7) may be directly reacted with cyclopropylamine to produce the compound (3); or regarding the compound (7) where $R^2$ is hydrogen,

[2] the compound may be condensed with cyclopropylamine using a dehydrating condensing agent, or

[3] the compound may be derived into an acid halide or a mixed acid anhydride, and then reacted with cyclopropylamine.

First, the method of directly reacting the compound with cyclopropylamine to produce the compound (3) (method [1]), is described.

An amount of cyclopropylamine to be used is preferably 1 to 50 molar times, more preferably 1 to 20 molar times, relative to the compound (7).

A reaction temperature is preferably −20 to 200° C., more preferably 0 to 100° C., from a viewpoint of shortening a reaction time and increasing a yield.

A reaction time is preferably 5 minutes to 48 hours, more preferably 2 hours to 24 hours, from a viewpoint of increasing a yield.

A pressure during the reaction is preferably 1 to 20 atmospheres, more preferably 1 to 5 atmospheres.

Regarding a reaction solvent in the step, cyclopropylamine may be used; or ether solvents such as tetrahydrofuran, 1,4-dioxane and ethylene glycol dimethyl ether; alcohol solvents such as methanol and ethanol; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen-containing solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; phosphonic triamide solvents such as hexamethylphosphonic triamide may be used. Preferred are ethanol, tetrahydrofuran, toluene or the like. One of them may be singly used, or two or more may be used in combination. In case where two or more are used in combination, a blend ratio is not specifically limited. An amount of the reaction solvent to be used is preferably 50 times by weight or less, more preferably 20 times by weight or less, relative to the compound (7).

An addition method and an addition order for the compound (7), cyclopropylamine and a reaction solvent in the reaction are not specifically limited.

Next, described is the method of condensing the compound (7) where $R^2$ is hydrogen with cyclopropylamine by a dehydrating condensing agent (method [2]).

A dehydrating condensing agent includes, for example, dicyclohexylcarbodiimide, 1-ethyl-3-(3-dimethylaminopropyl)carbodiimide, 1-ethyl-3-(3-dimethylaminopropyl)carbodiimide hydrochloride, diisopropylcarbodiimide, 1-[bis(dimethylamino)methylene]-1H-1,2,3-triazolo(4,5-b)pyridinium 3-oxidohexafluorophosphate, and bromotris(pyrrolidino) phosphonium hexafluorophosphate. From a view point of easiness in a post-treatment after the reaction, use of 1-ethyl-3-(3-dimethylaminopropyl)carbodiimide or its hydrochloride is preferable.

An amount of a dehydrating condensing agent to be used may be 1 to 5 molar times, preferably 1 to 2 molar times, relative to the compound (7). An amount of an additive to be used may be 0.5 to 5 molar times, preferably 1 to 2 molar times, relative to the compound (7).

An amount of cyclopropylamine to be used is preferably 1 to 10 molar times, more preferably 1 to 4 molar times, relative to the compound (7).

A reaction solvent usable in the step includes ether solvents such as tetrahydrofuran, 1,4-dioxan and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen-containing solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; phosphonic triamide solvents such as hexamethylphosphonic triamide. Preferred are tetrahydrofuran, ethyl acetate, toluene, methylene chloride or the like. One of them may be singly used, or two or more may be used in combination. When a mixed solvent is used, a blend ratio is not specifically limited.

An amount of the reaction solvent to be used is preferably 50 times by weight or less, more preferably 20 times by weight or less, relative to the compound (7).

A reaction temperature is preferably −20 to 100° C., more preferably 0 to 70° C., from a viewpoint of shortening a reaction time and increasing a yield.

A reaction time is preferably 5 minutes to 20 hours, more preferably 30 minutes to 5 hours, from a viewpoint of increasing a yield.

In the method, an additive may be further added for a purpose of attaining any of shortening a reaction time, increasing a reaction yield, preventing a side product or lowering a reaction temperature.

An additive includes, for example, N-hydroxysuccinimide, 1-hydroxybenzotriazole, 6-chloro-1-hydroxybenzotriazole, 3,4-dihydro-3-hydroxy-4-oxo-1,2,3-benzotriazine, 1-hydroxy-7-azabenzotriazole, 4-(dimethylamino)pyridine or the like.

An addition method and an addition order for the compound (7), a dehydrating condensing agent, an additive, cyclopropylamine and a reaction solvent in the reaction are not specifically limited.

Next, described is a method of converting the compound (7) where $R^2$ is hydrogen into an acid halide or a mixed acid anhydride thereof, followed by reacting with cyclopropylamine (method [3]), is described.

An acid halide includes an acid chloride, an acid bromide, an acid fluoride or the like. Preferred is an acid chloride. A method for preparing the acid halide is not specifically limited; and for example, the halide may be prepared according to a method described in Experimental Chemistry, Lecture 16, 5th Ed., edited by the Chemical Society of Japan, published by Maruzen, pp. 101-104. For example, the acid chloride may be prepared by reacting the compound (7) with thionyl chloride. An amount of thionyl chloride to be used is preferably 1 to 10 molar times, more preferably 1 to 4 molar times, relative to the compound (7).

A mixed acid anhydride includes anhydrides with a carboxylic acid such as acetic acid, trifluoroacetic acid, pivalic acid and benzoic acid; anhydrides with a sulfonic acid such as methanesulfonic acid, p-toluenesulfonic acid and m-nitrobenzenesulfonic acid; anhydrides with an alkoxycarboxylic acid such as methoxycarboxylic acid, ethoxycarboxylic acid, isopropoxycarboxylic acid, tert-butoxycarboxylic acid, benzyloxycarboxylic acid and phenoxycarboxylic acid. Preferred are an anhydride with pivalic acid; and an anhydride with an alkoxycarboxylic acid such as methoxycarboxylic acid, ethoxycarboxylic acid, isopropoxycarboxylic acid, tert-butoxycarboxylic acid, benzyloxycarboxylic acid and phenoxycarboxylic acid; and more preferred is an anhydride with pivalic acid or an anhydride with ethoxycarboxylic acid.

A method for preparing a mixed acid anhydride is not specifically limited; however, for example, the compound (7) is converted into an acid chloride thereof according to the above method, and then the acid chloride is reacted with a carboxylic acid salt according to a method described in Experimental Chemistry, Lecture 16, 5th Ed., edited by the Chemical Society of Japan, published by Maruzen, pp. 107-117, to obtain a mixed acid anhydride thereof. The carboxylic acid salt is preferably a sodium salt or a potassium salt. An amount of the carboxylic acid salt to be used is preferably 1 to 5 molar times, more preferably 1 to 2 molar times, relative to the acid chloride of the compound (7).

An anhydride with a carboxylic acid, especially an anhydride with pivalic acid, may also be prepared by reacting the compound (7) and pivaloyl chloride in a presence of a base mentioned hereinafter.

Further, an anhydride with an alkoxycarboxylic acid may be prepared by reacting the compound (7) with an alkoxycarbonyl chloride such as methoxycarbonyl chloride, ethoxycarbonyl chloride, isopropoxycarbonyl chloride, benzyloxycarbonyl chloride and phenoxycarbonyl chloride; or a dialkyl dicarbonate such as diethyl dicarbonate, di-tert-butyl dicarbonate and dibenzyl dicarbonate, in a presence of a base mentioned hereinafter. Preferred is an anhydride with an alkoxycarboxylic acid prepared by reacting the compound with methoxycarbonyl chloride, ethoxycarbonyl chloride, isopropoxycarbonyl chloride or benzyloxycarbonyl chloride.

Such a base is not specifically limited; but is preferably a tertiary amine, for example, triethylamine, tri-n-butylamine, N-methylmorpholine, N-methylpiperidine, diisopropylethylamine, pyridine, N,N-dimethylaminopyridine or the like. More preferred is triethylamine. An amount of a base to be used is preferably 1 to 10 molar times, more preferably 1 to 4 molar times, relative to the compound (7).

An amount of an alkoxycarbonyl chloride or a dialkyl dicarbonate to be used is preferably 1 to 10 molar times, more preferably 1 to 4 molar times, relative to the compound (7).

In the method [3], an amount of cyclopropylamine to be used is preferably 1 to 10 molar times, more preferably 1 to 4 molar times, relative to the compound (7).

A reaction solvent in the step is exemplified by the same as the solvent used in condensing the compound (7) where $R^2$ is hydrogen and cyclopropylamine with a dehydrating condensing agent. One of them may be singly used, or two or more may be used in combination. When a mixed solvent is used, a blend ratio is not specifically limited. An amount of the reaction solvent to be used is preferably 50 times by weight or less, more preferably 20 times by weight or less, relative to the compound (7).

A reaction temperature is preferably −50 to 80° C., more preferably −25 to 50° C., from a viewpoint of shortening a reaction time and increasing a yield.

A reaction time is preferably 5 minutes to 20 hours, more preferably 30 minutes to 5 hours, from a viewpoint of increasing a yield.

An addition method and an addition order for the compound (7), a base, an alkoxycarbonyl chloride or a dialkyl dicarbonate, cyclopropylamine and a reaction solvent in the reaction are not specifically limited.

A treatment after the each reaction of method [1] to [3] may be any ordinary treatment for collecting a product from a reaction mixture. For example, a reaction mixture after the reaction is neutralized by adding thereto water and optionally an aqueous alkaline solution such as an aqueous sodium hydroxide solution and an aqueous sodium hydrogencarbonate solution or an aqueous acid solution such as an aqueous hydrochloric acid solution and an aqueous sulfuric acid solution thereto; and then is extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, to obtain an intended product. The thus-obtained product may have a sufficient purity enough for use in the subsequent step; however, a purity of the product may be further increased by an ordinary purification method of crystallization, fractional distillation, column chromatography or the like for a purpose of further increasing a yield in the subsequent step or increasing a purity of the compound to be obtained in the subsequent step.

Needless-to-say, a method containing a step of hydrolyzing the compound (7) where $R^2$ is not a hydrogen atom into the compound (7) where $R^2$ is hydrogen; and then condensing the compound with cyclopropylamine using a dehydrating condensing agent, or converting the compound into an acid halide or a mixed acid anhydride thereof, followed by reaction with cyclopropylamine, is within the scope of the present invention.

In the case, a method of hydrolyzing the compound (7) includes, for example, a method of using an aqueous solution of an alkali metal hydroxide such as lithium hydroxide, sodium hydroxide, cesium hydroxide and potassium hydroxide. The hydrolysis may be carried out along with a cyclization described in the section of the step 2.

An amount of an alkali metal hydroxide to be used is preferably 1 to 50 molar times, more preferably 1 to 10 molar times, relative to the compound (7).

An amount of water to be used is preferably 1 to 50 times by weight, more preferably 1 to 10 times by weight, relative to an alkali metal hydroxide.

A reaction temperature is preferably 0 to 100° C., more preferably 20 to 70° C., from a viewpoint of shortening a reaction time and increasing a yield.

A reaction time is preferably 5 minutes to 20 hours, more preferably from 30 minutes to 5 hours, from a viewpoint of increasing a yield.

Regarding a treatment after the reaction, for example, a reaction mixture may be concentrated directly by operation of heating under reduced pressure or the like to isolate an optically-active epoxycarboxylic acid salt represented by the following formula (13):

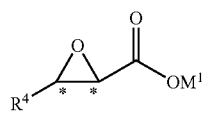

(13)

as a solid. In the above, * and $R^4$ are the same as above. $M^1$ represents an alkali metal such as lithium, sodium, potassium and cesium, preferably sodium and potassium. The compound (13) is a novel compound not described in literatures.

As a method of isolating the compound (13), employable is a method containing to evaporate away a reaction solvent from a reaction mixture by heating under reduced pressure or the like for drying into a solid, or containing to add a solvent such as methanol, ethanol, isopropanol, acetone and acetonitrile to a reaction mixture to thereby precipitate and isolate a crystal.

An optically-active epoxycarboxylic acid salt represented by the formula (13) may be produced according to the above method; but needless-to-say, the salt may also be produced by reacting a compound of the formula (7) where $R^2$ is hydrogen with an aqueous solution of an alkali metal hydroxide.

An isolated compound (13) may be neutralized with an aqueous acid solution such as an aqueous hydrochloric acid solution and an aqueous sulfuric acid solution added thereto, and extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, thereby obtaining the compound (7) where $R^2$ is hydrogen. The compound (13) may not be isolated and be processed for a post-treatment to give the compound (7) where $R^2$ is hydrogen.

An anhydride with an alkoxycarboxylic acid may be directly prepared, not via the compound (7) where $R^2$ is hydrogen, by reacting an optically-active epoxycarboxylic acid salt represented by the formula (13) with pivaloyl chloride, alkoxycarbonyl chloride or dialkyl dicarbonate. A reaction of the anhydride with an alkoxycarboxylic acid and cyclopropylamine is the same as above.

Regarding a stereochemistry of the compound (3) obtained in the step, a stereochemistry of the compound (7) is maintained. Specifically, (2S,3R) or (2R,3S) is preferable for the stereochemistry of the compound (3).

Step 4

In the step, an optically-active epoxyamide derivative represented by the formula (3) is reacted with a nitrile represented by the following formula (4):

in a presence of an acid catalyst to produce an optically-active oxazolinamide derivative represented by the following formula (1):

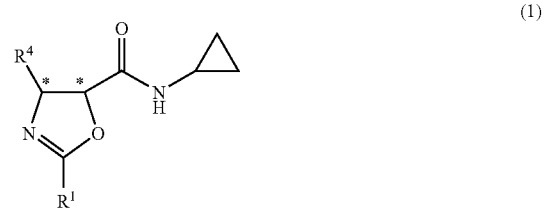

In the above, * and $R^4$ are the same as above. $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent. The substituent includes, for example, a halogen atom such as a fluorine atom, a chlorine atom, a bromine atom and an iodine atom; and the number of the substituent may be 0 to 3. Specifically, $R^1$ includes a methyl group, an ethyl group, an n-propyl group, an isopropyl group, an n-butyl group, a tert-butyl group, a chloromethyl group, a dichloromethyl group, a trichloromethyl group, a vinyl group, an allyl group, a phenyl group and a benzyl group. Preferred is a methyl group, an ethyl group, an isopropyl group, a chloromethyl group, a phenyl group or a benzyl group. More preferred is an isopropyl group.

The compound (1) obtained in the step is a novel compound not described in literatures, which is useful as an intermediate for a medicine. The compound (3) for use herein may be one produced in the step 3, or may be obtained separately.

An acid catalyst includes, for example, Lewis acids such as boron trifluoride diethyl ether complex, lithium perchlorate, scandium chloride, zinc chloride, magnesium chloride, aluminium chloride, aluminium triflate, titanium tetrachloride, tin tetrachloride, hafnium chloride, zirconium chloride, ytterbium triflate, scandium triflate, titanium propoxide, zirconium propoxide and aluminium propoxide; and Broensted acids such as sulfuric acid, hydrogen chloride, hydrogen bromide, nitric acid, trifluoromethanesulfonic acid, methanesulfonic acid, p-toluenesulfonic acid, trifluoroacetic acid and trichloroacetic acid. Preferred is boron trifluoride diethyl ether complex, zinc chloride, magnesium chloride, aluminium chloride, titanium tetrachloride, sulfuric acid, hydrogen chloride, hydrogen bromide, trifluoromethanesulfonic acid, methanesulfonic acid, p-toluenesulfonic acid or trifluoroacetic acid.

An amount of an acid to be used is preferably 0.01 to 10 molar times, more preferably 0.1 to 5 molar times, relative to the compound (3).

An amount of the nitrile (4) to be used is preferably 1 to 100 molar times, more preferably 1 to 50 molar times, relative to the compound (3).

A reaction temperature is preferably −20 to 80° C., more preferably −10 to 50° C., from a viewpoint of shortening a reaction-time and increasing a yield.

A reaction time is preferably 5 minutes to 48 hours, more preferably 2 hours to 24 hours, from a viewpoint of increasing a yield.

As a reaction solvent in the step, the nitrile (4) may be used; or ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; halogen-containing solvents such as methylene chloride and chloroform may also be used. Preferred are methylene chloride, toluene or the like. One of them may be singly used, or two or more may be used in combination. In case where two or more are used in combination, a blend ratio is not specifically limited.

An amount of a reaction solvent to be used is preferably 50 times by weight or less, more preferably 20 times by weight or less, relative to the compound (3).

An addition method and an addition order for the compound (3), the nitrile (4), an acid catalyst and a reaction solvent in the reaction are not specifically limited.

A treatment after the reaction may be any ordinary treatment for collecting a product from a reaction mixture. For example, a reaction mixture after the reaction is neutralized by adding thereto water and optionally an aqueous alkaline solution such as an aqueous sodium hydroxide solution and an aqueous sodium hydrogencarbonate solution; and then is extracted with an ordinary extraction solvent, for example, ethyl acetate, diethyl ether, methylene chloride, toluene and hexane. A reaction solvent and an extraction solvent are removed from the obtained extract through operation of heating under reduced pressure or the like, to obtain an intended product. The thus-obtained product may have a sufficient purity enough for use in the subsequent step; however, a purity of the product may be further increased by an ordinary purification method of crystallization, fractional distillation, column chromatography or the like for a purpose of further increasing a yield in the subsequent step or increasing a purity of the compound to be obtained in the subsequent step.

Regarding a stereochemistry, the reaction with a starting material of the compound (3) goes on along with inversion at a 3-position of the compound in the step. A main chain on IUPAC nomenclature of the starting material of the compound (3) differs from that of a reaction product of the compound (1); and therefore, the 3-position carbon of the compound (3) corresponds to a 4-position carbon of the compound (1), and a 2-position carbon of the compound (3) corresponds to a 5-position carbon of the compound (1).

Accordingly,
the (4S,5S) compound (1) is obtained from the (2S,3R) compound (3);
the (4R,5S) compound (1) is obtained from the (2S,3S) compound (3);
the (4R,5R) compound (1) is obtained from the (2R,3S) compound (3);
the (4S,5R) compound (1) is obtained from the (2R,3R) compound (3).

A preferable stereochemistry of the compound (1) is (4S,5S) or (4R,5R).

Step 5

In the step, an optically-active oxazolinamide derivative represented by the formula (1) is processed for selective acid hydrolysis or acid alcoholysis at an oxazoline ring thereof, thereby producing an optically-active 3-amino-2-hydroxypropionic cyclopropylamide derivative represented by the following formula (2):

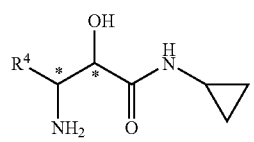

(2)

or salt thereof. In the above, * and $R^4$ are the same as above.

A salt of the formula (2) is not specifically limited; but includes salts with a Broensted acid such as sulfuric acid, hydrogen chloride, hydrogen bromide, nitric acid, trifluoromethanesulfonic acid, methanesulfonic acid, p-toluenesulfonic acid, trifluoroacetic acid and trichloroacetic acid. Preferred are salts with hydrogen chloride, hydrogen bromide or methanesulfonic acid; and more preferred is salt with hydrogen chloride.

The compound (1) for use herein may be one produced in the step 4 or in the step 7 to be mentioned hereinafter, or may be obtained separately.

In the step, a compound represented by the following formula (14):

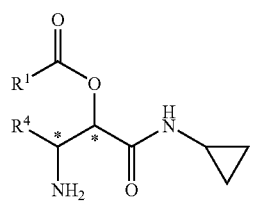

(14)

is firstly generated by a hydrolysis or alcoholysis with an acid of the compound (1), and then only the ester group of the compound (14) is hydrolyzed or alcoholyzed. In the result, the compound (1) is converted into the intended compound (2) without being accompanied by decomposition of a cyclopropylamide skeleton.

In the above, an acid includes, for example, Lewis acids and Broensted acids exemplified as an acid catalyst in the step 4. Preferred is sulfuric acid, hydrogen chloride, hydrogen bromide or methanesulfonic acid; more preferred is hydrogen chloride, hydrogen bromide or methanesulfonic acid; and even more preferred is hydrogen chloride. The acid may be used as it is; or may be dissolved in water and the aqueous solution of the acid may be used.

An amount of the acid to be used is preferably 0.01 to 50 molar times, more preferably 0.1 to 20 molar times, relative to the compound (1).

A reaction solvent to be used in the step includes water; and alcohol solvents such as methanol, ethanol, n-propanol and isopropanol; and a mixed solvent thereof is also usable. Preferred are water, methanol, ethanol and isopropanol. In case where two or more are used in combination, a blend ratio is not specifically limited. An amount of the reaction solvent to be used is preferably 50 times by weight or less, more preferably 20 times by weight or less, relative to the compound (1).

A reaction temperature is preferably −50 to 90° C., more preferably −25 to 60° C., from a viewpoint of shortening a reaction time and increasing a yield.

A reaction time is preferably 5 minutes to 48 hours, more preferably 2 hours to 24 hours, from a viewpoint of increasing a yield.

An addition method and an addition order for the compound (1), an acid and a reaction solvent in the reaction are not specifically limited.

As a treatment after the reaction, any ordinary treatment for collecting a product from a reaction mixture may be carried out. For example, a reaction mixture after the reaction is neutralized by adding thereto water and optionally an aqueous alkaline solution such as an aqueous sodium hydroxide solution and an aqueous sodium hydrogencarbonate solution; and then extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, thereby obtaining an intended product. A reaction mixture after the reaction may be concentrated and dried to be a solid, or may be subjected to solvent substitution with an organic solvent such as methanol, ethanol, isopropanol, acetone, acetonitrile, toluene and tetrahydrofuran, to precipitate a salt with an acid of optically-active 3-amino-2-hydroxypropionic cyclopropylamide derivative as a crystal. The salt is collected through filtration to obtain the intended product. The thus-obtained product may have a sufficient purity enough for use in the subsequent step; however, for a purpose of further increasing a purity thereof, the product may be further processed according to an ordinary purification method of crystallization, fractional distillation, column chromatography or the like, to thereby increase a purity thereof.

Regarding a stereochemistry, the product may have a stereochemistry of a starting material directly as it is; however, A main chain on IUPAC nomenclature of the starting material of the compound (1) differs from that of the reaction product of the compound (2); and therefore, a 5-position carbon of the compound (1) corresponds to a 2-position carbon of the compound (2), and a 4-position carbon of the compound (1) corresponds to a 3-position carbon of the compound (2).

Accordingly,
the (2R,3S) compound (2) is obtained from the (4S,5R) compound (1);
the (2S,3S) compound (2) is obtained from the (4S,5S) compound (1);
the (2S,3R) compound (2) is obtained from the (4R,5S) compound (1);
the (2R,3R) compound (2) is obtained from the (4R,5R) compound (1).

A preferable stereochemistry of the compound (1) is (2S,3S) or (2R,3R).

Step 6

In the step, an optically-active epoxycarboxylic acid derivative represented by the formula (7) is reacted with a nitrile represented by the formula (4) in a presence of an acid catalyst to produce an optically-active oxazolinecarboxylic acid derivative represented by the following formula (5):

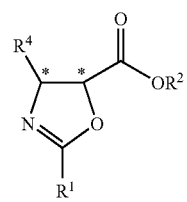

(5)

In the above, *, $R^1$, $R^2$ and $R^4$ are the same as above. The compound (5) obtained in the step is a novel compound not described in literatures, which is useful as an intermediate for a medicine. A method of obtaining the compound (7) is the same as that described for the step 3, and preferably, the compound (7) obtained in the step 2 is used herein.

A reaction condition is the same as a reaction condition in the step 4, and the starting material (7) may be used in place of (3) used in the step 4.

Regarding a stereochemistry, a reaction with the starting material of the compound (7) goes on along with inversion at a 3-position of the compound in the step. A main chain on IUPAC nomenclature of the starting material of the compound (7) differs from that of a reaction product of the compound (5); and therefore, the 3-position carbon of the compound (7) corresponds to a 4-position carbon of the compound (5), and a 2-position carbon of the compound (7) corresponds to a 5-position carbon of the compound (5).

Accordingly,
the (4S,5S) compound (5) is obtained from the (2S,3R) compound (7);
the (4R,5S) compound (5) is obtained from the (2S,3S) compound (7);
the (4R,5R) compound (5) is obtained from the (2R,3S) compound (7);
the (4S,5R) compound (5) is obtained from the (2R,3R) compound (7).

A preferable stereochemistry of the compound (1) is (4S,5S) or (4R,5R).

Step 7

In the step, an optically-active oxazolinecarboxylic acid derivative represented by the formula (5) is reacted with cyclopropylamine represented by the formula (6) to produce an optically-active oxazolinamide derivative represented by the formula (1). The compound (5) to be used herein may be one produced in the step 6, or may be obtained separately.

In the step, the compound (5) may be reacted directly with cyclopropylamine to produce the compound (1); or in case where $R^2$ is hydrogen, the compound may be reacted with cyclopropylamine using a dehydrating condensing agent, or the compound is derived into an acid halide or a mixed acid anhydride and then may be reacted with cyclopropylamine.

A reaction condition in the step is the same as a reaction condition in the step 3. In place of the starting material (7)

used in the step 3, (5) is used; and all the other conditions are the same as those described for the step 3.

Regarding a stereochemistry of the compound (1) obtained in the step, the compound has a stereochemistry of the compound (5) directly as it is. Specifically, a stereochemistry of the compound (1) is preferably (4S,5S) or (4R,5R).

Step 8

In the step, an oxazoline ring of an optically-active oxazolinamide derivative represented by the formula (1) is selectively alkali-hydrolyzed to produce a compound represented by a general formula (17):

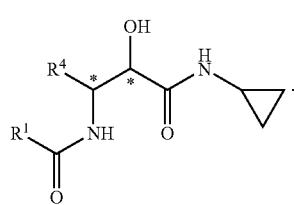

(17)

In the above, *, $R^1$ and $R^4$ are the same as above. The compound (17) obtained in the step is a novel compound not described in literatures, which is useful as an intermediate for a medicine. The compound (1) produced in the step 4 or 7 may be used herein, or the compound obtained separately may be used.

An alkali includes metal hydroxides such as lithium hydroxide, sodium hydroxide, potassium hydroxide and magnesium hydroxide; metal carbonates such as lithium carbonate, sodium carbonate and potassium carbonate; and metal hydrogencarbonates such as lithium hydrogencarbonate, sodium hydrogencarbonate and potassium hydrogencarbonate. Preferred are metal hydrogencarbonates such as lithium hydrogencarbonate, sodium hydrogencarbonate and potassium hydrogencarbonate; and more preferred is sodium hydrogencarbonate. An amount of the alkali to be used is preferably 1 to 50 molar times, more preferably 1 to 10 molar times, relative to the compound (1).

A solvent to be used in the step is water; and an organic solvent may be further added for a purpose of increasing a solubility of a starting material and a product to thereby accelerate a reaction speed. The organic solvent includes, for example, ether solvents, alcohol solvents, ester solvents, hydrocarbon solvents, ketone solvents, nitrile solvents, halogen-containing solvents, amide solvents, sulfoxide solvents, urea solvents, and phosphonic triamide solvents. More specific examples of the solvent are the same as those exemplified in the step 3. Preferred are methanol, ethanol, propanol, isopropanol, tetrahydrofuran, acetonitrile or the like. One of them may be singly used, or two or more may be used in combination. When a mixed solvent is used, a blend ratio is not specifically limited.

An amount of water to be used is preferably 50 times by weight or less, more preferably 20 times by weight or less, relative to the compound (1). An amount of the organic solvent to be used is preferably 50 times by weight or less, more preferably 20 times by weight or less, relative to the compound (1).

A reaction temperature is preferably −50 to 90° C., more preferably −25 to 60° C., from a viewpoint of shortening a reaction time and increasing a yield.

A reaction time is preferably 5 minutes to 48 hours, more preferably 2 hours to 24 hours, from a viewpoint of increasing a yield.

An addition method and an addition order for the compound (1), an alkali, water and an organic solvent in the reaction are not specifically limited.

As a treatment after the reaction, any ordinary treatment for collecting a product from a reaction mixture may be carried out. For example, a reaction mixture after the reaction is neutralized by adding thereto water and optionally an aqueous acid solution such as an aqueous hydrochloric acid solution and an aqueous sulfuric acid solution, and then extracted with an ordinary extraction solvent, for example, ethyl acetate, diethyl ether, methylene chloride, toluene or hexane. A reaction solvent and an extraction solvent are removed from obtained extract through operation of heating under reduced pressure or the like, to thereby obtain an intended product. The thus-obtained product may have a sufficient purity enough for use in the subsequent step; however, for a purpose of further increasing a yield in the subsequent step or increasing a purity of the compound to be obtained in the subsequent step, a purity of the product may be further increased by an ordinary purification method of crystallization, fractional distillation, column chromatography or the like, to thereby increase a purity thereof.

Regarding a stereochemistry, a stereochemistry of a starting material is maintained in a product; however, a main chain on IUPAC nomenclature of the starting material of the compound (1) differs from that of the reaction product of the compound (17); and therefore, a 5-position carbon of the compound (1) corresponds to a 2-position carbon of the compound (17), and a 4-position carbon of the compound (1) corresponds to a 3-position carbon of the compound (17).

Accordingly, the (2R,3S) compound (17) is obtained from the (4S,5R) compound (1);

the (2S,3S) compound (17) is obtained from the (4S,5S) compound (1);

the (2S,3R) compound (17) is obtained from the (4R,5S) compound (1);

the (2R,3R) compound (17) is obtained from the (4R,5R) compound (1).

A preferable stereochemistry of the compound (1) is (2S, 3S) or (2R,3R).

Step 9

In the step, a 3-position amide group of a compound represented by the formula (17) is selectively hydrolyzed, i.e. deprotected, to produce an optically-active 3-amino-2-hydroxypropionic cyclopropylamide derivative represented by the formula (2) or salt thereof. In the above, * is the same as above. The compound (17) produced in the step 8 or the step 11 to be mentioned later may be used herein, or the compound obtained separately may be used.

Regarding a reaction condition in the step, for example, the step may be carried out according to a method described in PROTECTIVE GROUPS in ORGANIC SYNTHESIS THIRD EDITION, by Greene Wuts, published by WILEY-INTERSCIENCE, pp. 550-572. However, when a strong acid or a strong base is used at high temperatures, a cyclopropylamide skeleton may be decomposed; and therefore, the deprotection is preferably carried out under a mild condition. Regarding the condition, for example, a chloroacetyl group may be selectively deprotected through reaction with thiourea. In the case, an amount of thiourea to be used is preferably 1 to 5 molar times, more preferably 1 to 2 molar times, relative to the compound (17).

A solvent to be used in the step is not specifically limited; but, includes, for example, water, ether solvents, alcohol solvents, ester solvents, hydrocarbon solvents, ketone solvents, nitrile solvents, halogen-containing solvents, amide solvents, sulfoxide solvents, urea solvents and phosphonic triamide solvents. More specific examples of the solvent is the same as those exemplified in the step 3. Preferred are water, methanol, ethanol, propanol, isopropanol, tetrahydrofuran, acetonitrile, toluene or the like. One of them may be singly used, or two or more may be used in combination. When a mixed solvent is used, a blend ratio is not specifically limited. An amount of the solvent to be used is preferably 50 times by weight or less, more preferably 20 times by weight or less, relative to the compound (17). An amount of the organic solvent to be used is preferably 50 times by weight or less, more preferably 20 times by weight or less, relative to the compound (17).

A reaction temperature is preferably −50 to 90° C., more preferably −25 to 60° C., from a viewpoint of shortening a reaction time and increasing a yield.

A reaction time is preferably 5 minutes to 48 hours, more preferably 2 hours to 24 hours, from a viewpoint of increasing a yield.

The step may also be carried out under a mild condition using an enzyme. In a reaction with an enzyme having an ability to selectively hydrolyze a 3-position amide group of the compound (17), preferably employed is a method of dissolving or dispersing the compound (17) and the enzyme having the ability of hydrolysis in an aqueous medium, and reacting them, from a viewpoint of smooth reaction and easiness in operation.

An aqueous solvent for hydrolysis must be so controlled as to have a pH suitable for an enzyme reaction, depending on a kind of the enzyme having an ability of hydrolysis. A pH range may be generally 6 to 12 or so, more preferably 7 to 10 or so. The pH control may be carried out by use of an aqueous buffer solution having a predetermined pH as an aqueous solvent. The aqueous buffer solution includes, for example, an aqueous buffer solution of an inorganic salt, such as an aqueous solution of an alkali metal phosphate, e.g. an aqueous sodium phosphate solution or an aqueous potassium phosphate solution; and an aqueous buffer solution of an organic acid salt such as an alkali metal acetate, e.g. an aqueous sodium acetate solution or an aqueous potassium acetate solution. For keeping the pH of the reaction system at a pH suitable for hydrolysis, a pH controlling agent, for example, a base such as an aqueous sodium hydroxide solution and an aqueous sodium hydrogencarbonate solution, or an acid such as hydrochloric acid and sulfuric acid, may be added in the initial stage of and/or during the hydrolysis.

An enzyme to be used is not specifically limited; but may be any one having an ability of selective hydrolysis of a 3-position amide group of the compound (17), and includes, for example, amidase. Preferred is penicillin amidase. An amount of the enzyme to be used is preferably 0.0001 to 3 times by weight, more preferably 0.001 to 1 time by weight, relative to the compound (17).

A preferable reaction temperature is generally within a range of 5 to 65° C., more preferably within a range of 20 to 50° C., since a stability of an enzyme lay lower and the enzyme may deactivate when the temperature is too high, but on the other hand, a reaction speed may lower when the temperature is too low.

A reaction time may vary depending on a kind and an amount of an enzyme used, a reaction temperature and others; and is preferably 5 minutes to 120 hours, more preferably 30 minutes to 48 hours.

An addition method and an addition order for reactants in the reaction are not specifically limited.

As a treatment after the reaction, any ordinary treatment for collecting a product from a reaction mixture may be carried out. For example, a reaction mixture after the reaction is neutralized by adding thereto water and optionally an aqueous acid solution such as an aqueous hydrochloric acid solution and an aqueous sulfuric acid solution, and then extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, thereby obtaining an intended product. The thus-obtained product may have a sufficient purity enough for use in the subsequent step; however, for a purpose of further increasing a purity thereof, the product may be further processed according to an ordinary purification method of crystallization, fractional distillation, column chromatography or the like, to thereby increase a purity thereof.

Regarding a stereochemistry, a stereochemistry of a starting material is maintained in the product.

Step 10

In the step, an optically-active oxazolinecarboxylic acid derivative represented by the formula (5) is hydrolyzed with an alkali to produce a compound represented by the following formula (16):

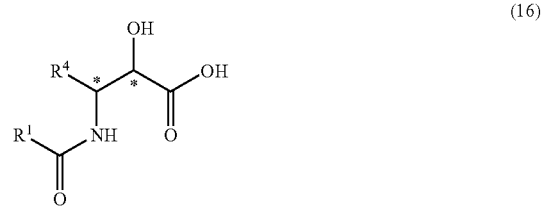

(16)

In the above, *, $R^1$ and $R^4$ are the same as above. The compound (5) produced in the step 6 may be used herein, or the compound obtained separately may be used.

A reaction condition in the step is the same as a reaction condition in the step 8. In place of the starting material (1) used in the step 8, the compound of formula (5) is used; and all the other conditions are the same as those described for the step 8.

Regarding a stereochemistry, a stereochemistry of a starting material is maintained in a product. However, a main chain on IUPAC nomenclature of the starting material of the compound (5) differs from that of the reaction product of the compound (16); and therefore, a 5-position carbon of the compound (5) corresponds to a 2-position carbon of the compound (16), and a 4-position carbon of the compound (5) corresponds to a 3-position carbon of the compound (16).

Accordingly, the (2R,3S) compound (16) is obtained from the (4S,5R) compound (5);

the (2S,3S) compound (16) is obtained from the (4S,5S) compound (5);

the (2S,3R) compound (16) is obtained from the (4R,5S) compound (5);

the (2R,3R) compound (16) is obtained from the (4R,5R) compound (5).

A preferable stereochemistry of the compound (1) is (2S, 3S) or (2R,3R).

Step 11

In the step, a compound of the formula (16) is reacted with a cyclopropylamine of the formula (6) to produce a compound of the formula (17). In the above, *, $R^1$ and $R^4$ are the same as above. The compound (16) produced in the step 10 may be used herein, or the compound obtained separately may be used.

In the step, the compound (16) may be directly reacted with cyclopropylamine; but preferably, the compound (16) and cyclopropylamine are condensed with a dehydrating condensing agent, or the compound (16) is derived into an acid halide or a mixed acid anhydride thereof and then reacted with cyclopropylamine.

A reaction condition for condensing the compound (16) and cyclopropylamine with a dehydrating condensing agent or for converting the compound (16) into an acid halide or a mixed acid anhydride thereof followed by reacting the halide or anhydride with cyclopropylamine is the same as a reaction condition described for the step 3. In place of the starting compound (7) where $R^2$ is a hydrogen atom in the step 3, the compound (16) is used.

Regarding a stereochemistry of the compound (17) obtained in the step, a stereochemistry of the compound (16) is maintained in the compound (17). Specifically, a stereochemistry of the compound (17) is preferably (2S,3S) or (2R,3R).

Step 12

In the step, an optically-active oxazolinecarboxylic acid derivative represented by the formula (5) is hydrolyzed with an acid and then a 3-position amino group thereof is carbamate-protected to produce an optically-active 3-amino-2-hydroxypropionic acid derivative represented by the following formula (12):

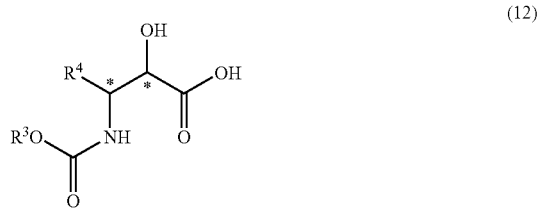

(12)

In the above, * and $R^4$ are the same as above. $R^3$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent. The substituent includes, for example, a halogen atom such as a fluorine atom, a chlorine atom, a bromine atom and an iodine atom; and a nitro group. The number of the substituent may be 0 to 3. Specifically, for example, the substituent is a methyl group, an ethyl group, an isopropyl group, a tert-butyl group, an allyl group, a phenyl group or a benzyl group; and preferred is a tert-butyl group or a benzyl group. The compound (5) produced in the step 6 may be used herein, or the compound obtained separately may be used.

An acid for use for hydrolysis includes mineral acids such as hydrochloric acid, hydrobromic acid, sulfuric acid and nitric acid; sulfonic acids such as methanesulfonic acid and p-toluenesulfonic acid; and carboxylic acids such as formic acid, acetic acid and trifluoroacetic acid. Preferred are mineral acids such as hydrochloric acid, hydrobromic acid, sulfuric acid and nitric acid; and more preferred is hydrochloric acid. An amount of the acid to be used is preferably 1 to 50 molar times, more preferably 2 to 20 molar times, relative to the compound (5).

A solvent for use in the step is water; but an organic acid may be further added for a purpose of dissolving a starting material and shortening a reaction time. The organic solvent includes, for example, solvents exemplified in the step 3. Preferred are methanol, ethanol, n-propanol, isopropanol, tetrahydrofuran, acetonitrile or the like. One of them may be singly used, or two or more may be used in combination. When a mixed solvent is used, a blend ratio is not specifically limited. An amount of the reaction solvent to be used is preferably 50 times by weight or less, more preferably 20 times by weight or less, relative to the compound (5).

A reaction temperature is preferably −20 to 120° C., more preferably 0 to 100° C., from a viewpoint of shortening a reaction time and increasing a yield.

A reaction time is preferably 5 minutes to 48 hours, more preferably 2 hours to 24 hours, from a viewpoint of increasing a yield.

An addition method and an addition order for the compound (5), an acid, water and an organic solvent in the reaction are not specifically limited.

Next, a method for carbamate protection of a 3-position amino group is described. A method of carbamate protection of the 3-position amino group is not specifically limited, and may be any ordinary protection method. One example is described below.

First, after an acid hydrolysis of the compound (5), a reaction mixture is neutralized with a base added thereto. Next, a carbamate-protecting reagent is added with adding a base so as to keep pH of 7 to 13, or a base enough to keep pH of 7 to 13 is previously added; and a carbamate-protecting reagent is added thereto; and the reaction is carried out.

A carbamate-protecting reagent includes, for example, methoxycarbonyl chloride, ethoxycarbonyl chloride, isopropoxycarbonyl chloride, di-tert-butyl dicarbonate, allyloxycarbonyl chloride, phenoxycarbonyl chloride, benzyloxycarbonyl chloride, dibenzyl dicarbonate or the like. Preferred is di-tert-butyl dicarbonate. An amount of the carbamate-protecting reagent to be used is preferably 1 to 5 molar times, more preferably 1 to 2 molar times, relative to the compound (5).

A reaction temperature is preferably −20 to 120° C., more preferably 0 to 100° C., from a viewpoint of shortening a reaction time and increasing a yield.

A reaction time is preferably 5 minutes to 48 hours, more preferably 2 hours to 24 hours, from a viewpoint of increasing a yield.

As a treatment after the reaction, any ordinary treatment for collecting a product from a reaction mixture may be carried out. For example, a reaction mixture after the reaction is neutralized by adding thereto water and optionally an aqueous acid solution such as an aqueous hydrochloric acid solution and an aqueous sulfuric acid solution, and then extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, thereby obtaining an intended product. The thus-obtained product may have a sufficient purity enough for use in the subsequent step; however, for a purpose of further increasing a purity thereof, the product may be further processed according to an ordinary purification method of crystallization, fractional distillation, column chromatography or the like, to thereby increase a purity thereof.

Regarding a stereochemistry, a stereochemistry of a starting material is maintained in a product. However, a main chain on IUPAC nomenclature of a starting material of the compound (5) differs from that of a reaction product of the compound (12); and therefore, a 5-position carbon of the compound (5) corresponds to a 2-position carbon of the compound (12), and a 4-position carbon of the compound (5) corresponds to a 3-position carbon of the compound (12).

Accordingly, the (2R,3S) compound (12) is obtained from the (4S,5R) compound (5);

the (2S,3S) compound (12) is obtained from the (4S,5S) compound (5);

the (2S,3R) compound (12) is obtained from the (4R,5S) compound (5);

the (2R,3R) compound (12) is obtained from the (4R,5R) compound (5).

A preferable stereochemistry of the compound (1) is (2S, 3S) or (2R,3R).

Step 13

In the step, a compound of the formula (12) is condensed with a cyclopropylamine of the formula (6) to produce a compound represented by the following formula (15):

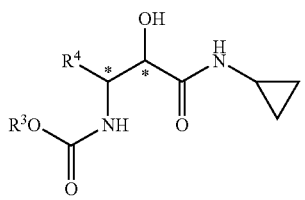

(15)

In the above, *, $R^3$ and $R^4$ are the same as above. The compound (12) produced in the step 12 may be used herein, or the compound obtained separately may be used.

In the step, the compound (12) may be directly reacted with cyclopropylamine; but preferably, the compound (12) and cyclopropylamine are condensed with a dehydrating condensing agent, or the compound (12) is derived into an acid halide or a mixed acid anhydride thereof and then reacted with cyclopropylamine.

The step may be carried out according to the same method for the step 3. In place of a starting material of the compound (7) used in the step 3, the compound (12) is used, and the reaction condition may be the same.

Regarding a stereochemistry thereof, a stereochemistry of the compound (12) is maintained in the compound (15) obtained in the step. Specifically, a stereochemistry of the compound (15) is preferably (2S,3S) or (2R,3R).

Step 14

In the step, a 3-position amino-protective group of a compound of the formula (15) is deprotected to produce an optically-active 3-amino-2-hydroxypropionic cyclopropylamide represented by the formula (2) or salt thereof. In the above, * and $R^4$ are the same as above. The compound (15) produced in the step 13 may be used herein, or the compound obtained separately may be used.

A method of deprotection may be suitably selected in accordance with a protective group. For example, when $R^3$ is a methyl group, an ethyl group or the like, hydrolysis may be carried out under any condition with acid or alkali; but when $R^3$ is a tert-butyl group, the compound is preferably hydrolyzed with acid. When $R^3$ is a benzyl group, the compound may be deprotected with hydrogen in a presence of a palladium catalyst.

A treatment after the reaction may be carried out suitably in accordance with a deprotection method. For example, in the case of acid hydrolysis, a reaction mixture after the reaction is neutralized optionally by adding thereto an aqueous alkaline solution such as an aqueous sodium hydroxide solution and an aqueous sodium hydrogencarbonate solution, and then extracted with an ordinary extraction solvent, for example, ethyl acetate, diethyl ether, methylene chloride, toluene or hexane. A reaction solvent and an extraction solvent are removed from the obtained extract through operation of heating under reduced pressure or the like, thereby obtaining an intended product. A reaction mixture after the reaction may be directly concentrated to dryness as such to thereby obtain the intended product as a salt of an acid, or the reaction mixture may be subjected to solvent substitution with an organic solvent such as methanol, ethanol, isopropanol, acetone, acetonitrile, tetrahydrofuran, toluene and the like thereby precipitating and isolating the product as a salt of the acid. The thus-obtained product may have a sufficient purity enough for use in the subsequent step; however, for a purpose of further increasing a yield in the subsequent step or increasing a purity of the compound to be obtained in the subsequent step, a purity of the product may be further increased by an ordinary purification method of crystallization, fractional distillation, column chromatography or the like.

Regarding a stereochemistry thereof, a stereochemistry of the compound (15) is maintained in the compound (2) obtained in the step. Specifically, the stereochemistry of the compound (2) is preferably (2S,3S) or (2R,3R).

EXAMPLES

The present invention is further specifically described with reference to the following Examples; however, the present invention should not be limited to these Examples.

Example 1

Production of ethyl (2S,3R)-3-propyl-2-oxiranecarboxylate

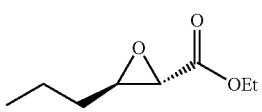

Ethyl (2R,3R)-2-chloro-3-hydroxyhexanoate (1.0 g, 5 mmol), ethanol (10 ml) and potassium carbonate (2.1 g, 15 mmol) were mixed, and the mixture was stirred at 15° C. for 14 hours. Methyl tert-butyl ether (20 ml) was added. The mixture was washed with water (10 ml) three times. The organic layer was concentrated under reduced pressure to obtain the title compound (0.83 g, yield: 100%).

$^1$H NMR (400 MHz, CDCl$_3$): δ 4.24-4.21 (m, 2H), 3.20 (d, 1H), 3.08-3.04 (dt, 1H), 1.72-1.62 (m, 2H), 1.61-1.50 (m, 2H), 1.28 (t, 3H), 0.98 (t, 3H)

Example 2

Production of methyl (2S,3R)-3-propyl-2-oxiranecarboxylate

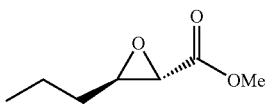

Methyl (2R,3R)-2-chloro-3-hydroxyhexanoate (0.9 g, 5 mmol), ethanol (10 ml) and potassium carbonate (2.1 g, 15 mmol) were mixed, and the mixture was stirred at 15° C. for 14 hours. Methyl tert-butyl ether (20 ml) was added. The mixture was washed with water (10 ml) three times. The organic layer was concentrated under reduced pressure to obtain the title compound (0.75 g, yield: 100%).

$^1$H NMR (400 MHz, CDCl$_3$): δ 3.81 (s, 3H), 3.23 (d, 1H), 3.18-3.15 (dt, 1H), 1.66-1.50 (m, 4H), 0.99 (t, 3H)

Example 3

Production of (2S,3R)-3-propyl-2-oxiranecarboxylic acid

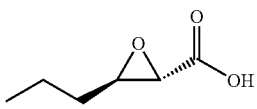

Ethyl (2R,3R)-2-chloro-3-hydroxyhexanoate (5.0 g, 22 mmol) and ethanol (15 ml) were mixed, and the mixture was cooled to 5° C. To the mixture, 20% sodium ethoxide/ethanol solution (8.3 g, 24 mmol) was gradually added. The mixture was stirred at room temperature for 1 hour. The precipitated inorganic salt was separated by filtration. Potassium hydroxide (1.24 g, 24 mmol) was added to the filtrate, and the mixture was stirred at room temperature for 14 hours. The solvent was evaporated away under reduced pressure, and water (15 ml) was added. The pH was adjusted to 1.8 with concentrated hydrochloric acid. The mixture was extracted with ethyl acetate (20 ml). The solvent was evaporated away under reduced pressure to obtain the title compound (2.33 g, yield: 65%).

$^1$H NMR (400 MHz, CDCl$_3$): δ 3.23 (d, 1H), 3.17 (dt, 1H), 1.72-1.51 (m, 4H), 0.98 (t, 3H)

Example 4

Production of (2S,3R)—N-cyclopropyl-3-propyl-2-oxiranecarboxamide

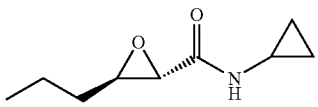

(2S,3R)-3-Propyl-2-oxiranecarboxylic acid (1.16 g, 7.8 mmol), methylene chloride (10 ml) and cyclopropylamine (8.5 equivalents) were mixed, and the mixture was cooled to 5° C. A methylene chloride solution (5 ml) of 1-ethyl-3-(3-dimethylaminopropyl)carbodiimide (2.23 g, 1.2 equivalents) was gradually added thereto, and the mixture was stirred for 2 hours from 5° C. up to room temperature. The organic layer was washed with water (5 ml), 1 N HCl (5 ml) and water (5 ml); and was dried with anhydrous magnesium sulfate. The inorganic products were separated by filtration, and the filtrate was concentrated under reduced pressure to obtain the title compound as a pale yellow solid (0.70 g, yield: 53%).

$^1$H NMR (400 MHz, CDCl$_3$): δ 6.15 (brs, 1H), 3.19 (d, 1H), 2.91-2.88 (m, 1H), 2.68 (dt, 1H), 1.65-1.48 (m, 4H), 0.99 (t, 3H), 0.79-0.77 (m, 2H), 0.52-0.48 (m, 2H)

Example 5

(4S,5S)—N-cyclopropyl-2-methyl-4-propyl-4,5-dihydro-1,3-oxazole-5-carboxamide

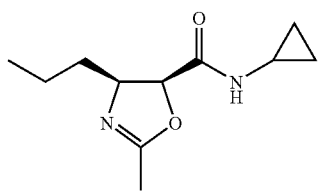

(2S,3R)—N-Cyclopropyl-3-propyl-2-oxiranecarboxylic acid (0.40 g, 2.4 mmol) and acetonitrile (4 ml) were mixed, and the mixture was cooled to 5° C. An acetonitrile solution (1 ml) of boron trifluoride diethyl ether complex (0.84 g, 6.2 mmol) was added, and the mixture was stirred for 2 hours at 5° C. and for 2 hours at room temperature. The reaction was quenched with saturated aqueous solution of sodium hydrogencarbonate (10 ml), and the mixture was extracted with ethyl acetate (25 ml). The organic layer was washed with water (5 ml), and the solvent was evaporated away under reduced pressure to obtain the title compound as a pale yellow solid (0.45 g, yield: 90%).

$^1$H NMR (400 MHz, CDCl$_3$): δ 6.32 (brs, 1H), 4.83 (d, 1H), 4.31 (dt, 1H), 2.75-2.71 (m, 1H), 2.04 (s, 3H), 1.72-1.66 (m, 1H), 1.55-1.51 (m, 1H), 1.42-1.37 (m, 1H), 0.94-0.89 (m, 1H), 0.92 (t, 3H), 0.84-0.80 (m, 2H), 0.57-0.52 (m, 2H)

Example 6

Production of (2S,3S)-3-amino-2-hydroxy-hexanoic cyclopropylamide hydrochloride

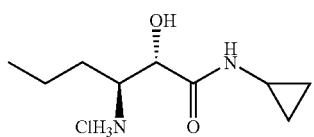

N-Cyclopropyl-2-methyl-4-propyl-4,5-dihydro-1,3-oxazole-5-carboxamide (0.10 g, 0.5 mmol), methanol (4 ml) and concentrated hydrochloric acid (0.5 ml, 5.5 mmol) were mixed, and the mixture was stirred at room temperature for 14 hours. The solvent was evaporated away under reduced pressure. Isopropanol (4 ml) was added to the obtained solid, and the mixture was stirred at room temperature for 10 minutes.

The crystal was collected by filtration, and was dried under reduced pressure to obtain the title compound as a white solid (0.03 g, yield: 28%).

$^1$H NMR (400 MHz, D$_2$O): δ 4.38 (d, 1H), 3.66-3.62 (m, 1H), 2.66-2.61 (m, 1H), 1.65-1.30 (m, 4H), 0.91 (t, 3H), 0.83-0.76 (m, 2H), 0.60-0.55 (m, 2H)

Example 7

Production of ethyl (4S,5S)-2-methyl-4-propyl-4,5-dihydro-1,3-oxazole-5-carboxylate

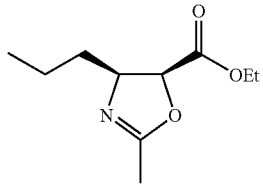

Acetonitrile (5 ml) was added to ethyl (2S,3R)-3-propyl-2-oxiranecarboxylate (0.8 g, 5 mmol). The mixture was cooled to 5° C., and boron trifluoride diethyl ether complex (0.4 g, 5.5 mmol) was gradually added dropwise thereto. The mixture was stirred at room temperature for 6 hours, and then saturated aqueous solution of sodium hydrogencarbonate (15 ml) was added thereto. The mixture was concentrated, and was extracted with ethyl acetate (20 ml). The organic layer was washed twice with water (10 ml), and the solvent was evaporated away under reduced pressure. The concentrated matter was purified by silica gel column chromatography to obtain the title compound as a colorless oil (0.69 g, yield: 65%).

$^1$H NMR (400 MHz, CDCl$_3$): δ 4.90 (d, 1H), 4.32-4.21 (m, 3H), 2.05 (s, 3H), 1.63-1.24 (m, 7H), 0.92 (t, 3H)

Example 8

Production of (2S,3S)—N-tert-butoxycarbonyl-3-amino-2-hydroxy-hexanoic acid

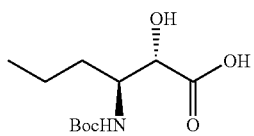

Ethyl (4S,5S)-2-methyl-4-propyl-4,5-dihydro-1,3-oxazole-5-carboxylate (0.68 g, 3 mmol) and 6 N hydrochloric acid (10 ml) were mixed, and the mixture was stirred at 100° C. for 14 hours. The mixture was cooled to 5° C., and the pH thereof was adjusted to 9.8. A toluene solution (1 ml) of di-tert-butyl dicarbonate (1 eq.) was added, and the mixture was stirred at room temperature for 2 hours. Water (10 ml) and ethyl acetate (20 ml) were added thereto, and the pH was adjusted to 2.3. The aqueous layer was removed, and the solvent was evaporated away under reduced pressure to obtain the title compound (0.71 g, yield: 78%).

$^1$H NMR (400 MHz, CDCl$_3$): δ 4.91 (d, 1H), 4.33 (d, 1H), 3.95 (ddt, 1H), 1.59-1.28 (m, 13H), 0.98 (t, 3H)

Example 9

Production of ethyl 2-chloro-3-hydroxyhexanoate

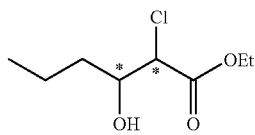

Benzene ruthenium(II) dichloride dimer (126 mg, S/C=50), (S)-2,2'-bisdiphenylphosphino-1,1'-binaphthyl (332 mg) and dimethylformamide (4 ml) were mixed, and nitrogen substitution was carried out after reducing the pressure. The mixture was stirred at 100° C. for 10 minutes to prepare a catalyst solution.

Ethyl 2-chloro-3-oxohexanoate (2.5 g, 13 mmol), methanol (7.5 ml) and water (0.75 ml) were mixed, and nitrogen substitution was carried out after reducing the pressure. The above catalyst solution was added thereto, and hydrogen substitution (3 atmospheres) was carried out under reduced pressure. The mixture was stirred at 70° C. for 14 hours. After the mixture was cooled to room temperature, the solvent was evaporated away under reduced pressure. The concentrated matter was purified by silica gel column chromatography to obtain the title compound as a colorless oil (1.83 g, yield: 72%) ((2S,3R):(2S,3S):(2R,3S):(2R,3R)=6.2:58.5:33.2:2.2).

Example 10

Production of ethyl (2R,3S)-3-propyl-2-oxiranecarboxylate

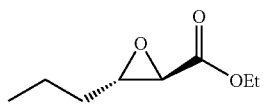

Ethyl 2-chloro-3-hydroxyhexanoate synthesized in Example 9 (0.8 g, 4 mmol), ethanol (3 ml) and 20% sodium ethoxide/ethanol solution (1.52 g, 1.1 equivalents) were mixed, and the mixture was stirred at room temperature for 30 minutes. Hexane (10 ml) was added, and the mixture was washed with water (10 ml×twice). After the mixture was dried with anhydrous magnesium sulfate, the inorganic salt was separated by filtration. The filtrate was concentrated under reduced pressure. The title compound was obtained as a colorless oil (0.9 g, yield: 87%, (2R,3S) was the main ingredient).

Example 11

Production of (2S,3R)-3-propyl-2-oxiranecarboxylic cyclopropylamide

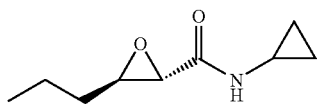

Methyl (2S,3R)-3-propyl-2-oxiranecarboxylate (0.26 g, 1.8 mmol), ethanol (1 ml) and cyclopropylamine (1.03 g, 18 mmol) were mixed, and the mixture was stirred at room temperature for 14 hours. Ethyl acetate (20 ml) was added, and the mixture was washed with 1 N HCl (5 ml) and water (5 ml). The solvent was evaporated away under reduced pressure to obtain the title compound as a pale yellow solid (0.17 g, yield: 55%).

Example 12

Production of (2S,3R)-3-propyl-2-oxiranecarboxylic cyclopropylamide

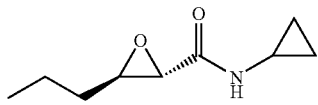

(2S,3R)-3-Propyl-2-oxiranecarboxylic acid (118 mg, 0.8 mmol), triethylamine (0.8 mmol) and tetrahydrofuran (2 ml) were mixed, and the mixture was cooled to −20° C. A tetrahydrofuran solution (1 ml) of ethoxycarbonyl chloride (86 mg, 0.8 mmol) was gradually added, and the mixture was stirred at the same temperature for 30 minutes. A tetrahydrofuran solution (1 ml) of cyclopropylamine (48 mg, 0.8 mmol) was gradually added dropwise, and the mixture was stirred at the same temperature for 2 hours and at room temperature for 2 hours. After the reaction was quenched with water (10 ml), ethyl acetate (10 ml) was added and the solvent was evaporated away under reduced pressure. The mixture was extracted with ethyl acetate (10 ml), and washed with water (5 ml). The solvent was evaporated away under reduced pressure to obtain the title compound as a colorless oil (0.10 g, yield: 76%).

Example 13

Production of methyl (4S,5S)-2-methyl-4-propyl-4,5-dihydro-1,3-oxazole-5-carboxylate

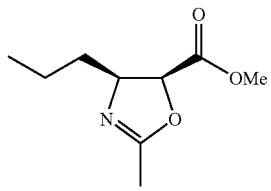

Acetonitrile (15 ml) was added to methyl (2S,3R)-3-propyl-2-oxiranecarboxylate (1.42 g, 9.8 mmol). The mixture was cooled to 5° C., and boron trifluoride diethyl ether complex (1.24 g, 11 mmol) was gradually added dropwise. The mixture was stirred at room temperature for 6 hours, and saturated aqueous solution of sodium hydrogencarbonate (20 ml) was added. The mixture was concentrated, and was extracted with ethyl acetate (30 ml). The organic layer was washed with water (10 ml×2), and the solvent was evaporated away under reduced pressure. The concentrated residue was purified by silica gel column chromatography to obtain the title compound as a colorless oil (1.23 g, yield: 76%).

$^1$H NMR (400 MHz, CDCl$_3$): δ 4.93 (d, 1H), 4.31 (dt, 1H), 3.81 (s, 3H), 2.05 (s, 3H), 1.63-1.31 (m, 4H), 0.93 (t, 3H)

Example 14

Production of (2S,3S)-3-amino-2-hydroxy-hexanoic acid hydrochloride

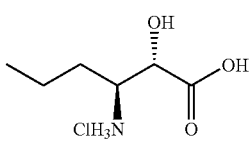

Methyl (4S,5S)-2-methyl-4-propyl-4,5-dihydro-1,3-oxazole-5-carboxylate (0.68 g, 3 mmol) and 6 N hydrochloric acid (10 ml) were mixed, and the mixture was stirred at 100° C. for 14 hours. The solvent was evaporated away under reduced pressure to obtain the title compound as a white solid (0.50 g, yield: 90%)

$^1$H NMR (400 MHz, D$_2$O): δ 4.37 (dd, 1H), 3.64 (dt, 1H), 1.68-1.27 (m, 4H), 0.98 (t, 3H)

Example 15

Production of methyl (2S,3S)-3-amino-2-hydroxyhexanoate hydrochloride

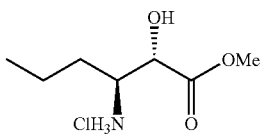

Methyl (4S,5S)-2-methyl-4-propyl-4,5-dihydro-1,3-oxazole-5-carboxylate (0.2 g, 1.1 mmol), methanol (2 ml) and concentrated hydrochloric acid (0.25 ml) were mixed, and the mixture was stirred at room temperature for 3 hours. The solvent was evaporated away under reduced pressure to obtain the title compound as a white solid (0.1 g, yield: 50%).

$^1$H NMR (400 MHz, D$^2$O): δ 4.67 (d, 1H), 3.90 (s, 3H), 3.79-3.74 (m, 1H), 1.79-1.61 (m, 1H), 1.58-1.24 (m, 4H), 0.92 (t, 3H)

Example 16

Reduction of ethyl 2-chloro-3-oxohexanoate with yeast

A liquid medium (pH 7.0) containing 4% of glucose, 0.3% of yeast extract, 1.3% of $KH_2PO_4$, 0.7% of $(NH_4)_2HPO_4$, 0.01% of NaCl, 0.08% of $MgSO_4.7H_2O$, 0.006% of $ZnSO_4.7H_2O$, 0.009% of $FeSO_4.7H_2O$, 0.0005% of $CuSO_4.5H_2O$, and 0.001% of $MnSO_4.4-5H_2O$ was prepared; the liquid medium was put into large-size test tubes in an amount of 5 ml each, and was sterilized with steam at 120° C. for 20 minutes. One platinum loop of yeast cells shown in Table 1 and Table 2 were inoculated into the liquid medium, and were incubated with shaking at 30° C. for 2 to 3 days. The cells were collected from the liquid medium by centrifugation or suction filtration, washed with water, and suspended in 0.1 M phosphate buffer (pH 5.5, 1 ml). Ethyl 2-chloro-3-oxohexanoate (1 mg) and glucose (10 mg) were added to the cell suspension (0.5 ml), and the suspension was shaken in a test tube sealed with a stopper at 30° C. for 24 hours. After the reaction, the suspension was extracted with ethyl acetate (1 ml), and the product in the extract was analyzed by GC to determine the yield (%), the diastereomer ratio (anti/syn) and the optical purity (% e.e.). The results are shown in Table 1 and Table 2.

The condition for analysis and the method for calculating the optical purity are as follows:

Analysis for Yield

Condition for GC analysis=capillary column: HP-5, $\phi$0.32 mm I.D.×30 m, manufactured by J & W Scientific; carrier gas: He 300 kPa; detector: FID; column temperature: 120° C.; detection time: ethyl 2-chloro-3-oxohexanoate 8.8 minutes, ethyl 2-chloro-3-hydroxyhexanoate 10.1-10.5 minutes Analysis for Diastereomer Ratio and Optical Purity Condition for GC analysis=capillary column: CHIRALDEX G-TA, $\phi$0.25 mm I.D.×30 m, manufactured by ASTEC; carrier gas: He 300 kPa; detector: FID; column temperature: 110° C.; detection time: ethyl (2R,3R)-2-chloro-3-hydroxyhexanoate 16.7 minutes, ethyl (2S,3S)-2-chloro-3-hydroxyhexanoate 17.8 minutes, ethyl (2R,3S)-2-chloro-3-hydroxyhexanoate 18.9 minutes, ethyl (2S,3R)-2-chloro-3-hydroxyhexanoate 20.7 minutes $$\text{Optical purity}(\%ee)=(A-B)/(A+B)\times 100$$

wherein, A and B each indicates the amount of the corresponding enantiomer; and A>B

TABLE 1

| Microorganisms | Yield (%) | Anti/Syn | Anti Form Optical purity (% e.e.) | Anti Form Configuration | Syn Form Optical purity (% e.e.) | Syn Form Configuration |
|---|---|---|---|---|---|---|
| *Ambrosiozyma philentoma* NBRC 1847 | 13 | 97/3 | 81 | (2R,3R) | | |
| *Brettanomyces custersianus* NBRC 1585 | 50 | 100/0 | 93 | (2R,3R) | | |
| *Candida cantarellii* NBRC 1261 | 43 | 96/4 | 65 | (2R,3R) | 24 | (2S,3R) |
| *Candida etchellsii* NBRC 1229 | 62 | 100/0 | 58 | (2S,3S) | | |
| *Candida guilliermondii* NBRC 0454 | 19 | 67/33 | >99 | (2S,3S) | >99 | (2S,3R) |
| *Candida haemulonii* NBRC 10001 | 18 | 100/0 | 91 | (2R,3R) | | |
| *Candida lactiscondensi* NBRC 1286 | 57 | 100/0 | 53 | (2S,3S) | | |
| *Candida pini* NBRC 1327 | 32 | 100/0 | 86 | (2R,3R) | | |
| *Candida maris* NBRC 10003 | 18 | 97/3 | 57 | (2R,3R) | | |
| *Candida pararugosa* NBRC 0966 | 11 | 91/9 | 64 | (2R,3R) | >99 | (2S,3R) |
| *Candida oleophila* NBRC 1021 | 48 | 98/2 | 69 | (2S,3S) | >99 | (2R,3S) |
| *Candida stellata* NBRC 0701 | 70 | 100/0 | 85 | (2R,3R) | | |
| *Candida utilis* NBRC 0639 | 37 | 69/31 | 88 | (2S,3S) | >99 | (2S,3R) |
| *Candida zeylanoides* NBRC 0738 | 13 | 97/3 | 75 | (2R,3R) | >99 | (2R,3S) |
| *Candida fermentati* NBRC 0679 | 39 | 93/7 | 63 | (2S,3S) | 69 | (2S,3R) |
| *Cryptococcus terreus* NBRC 0727 | 44 | 100/0 | 76 | (2R,3R) | | |
| *Debaryomyces nepalensis* NBRC 0039 | 18 | 96/4 | 58 | (2R,3R) | | |
| *Debaryomyces carsonii* NBRC 0946 | 37 | 94/6 | 94 | (2S,3S) | >99 | (2R,3S) |
| *Debaryomyces robertsiae* NBRC 1277 | 14 | 93/7 | >99 | (2S,3S) | 31 | (2R,3S) |
| *Debaryomyces castellii* NBRC 1359 | 57 | 100/0 | 85 | (2S,3S) | | |
| *Debaryomyces polymorphus* ATCC 20280 | 41 | 85/15 | 67 | (2S,3S) | 34 | (2R,3S) |
| *Hanseniaspora valbyensis* NBRC 0115 | 70 | 86/14 | 73 | (2R,3R) | >99 | (2R,3S) |
| *Issatchenkia terricola* NBRC 0933 | 41 | 100/0 | 80 | (2R,3R) | | |
| *Kluyveromyces thermotolerans* NBRC 0662 | 18 | 81/19 | 87 | (2S,3S) | >99 | (2S,3R) |
| *Kluyveromyces lactis* var. *drosophilarum* NBRC 1012 | 31 | 100/0 | 84 | (2R,3R) | | |
| *Kluyveromyces lactis* var. *lactis* NBRC 0648 | 15 | 97/3 | 87 | (2R,3R) | >99 | (2R,3S) |
| *Kuraishia capsulata* NBRC 0721 | 22 | 95/5 | 61 | (2R,3R) | 29 | (2S,3R) |
| *Metschnikowia bicuspidata* var. *bicuspidata* NBRC 1408 | 30 | 91/9 | 50 | (2S,3S) | 47 | (2S,3R) |
| *Ogataea glucozyma* NBRC 1472 | 64 | 97/3 | 81 | (2R,3R) | >99 | (2S,3R) |
| *Pachysolen tannophilus* NBRC 1007 | 58 | 97/3 | 81 | (2R,3R) | 35 | (2S,3R) |

TABLE 2

| Microorganisms | Yield (%) | Anti/Syn | Anti Form Optical purity (% e.e.) | Configuration | Syn Form Optical purity (% e.e.) | Configuration |
|---|---|---|---|---|---|---|
| *Pichia bovis* NBRC 0872 | 29 | 90/10 | 64 | (2S,3S) | 42 | (2S,3R) |
| *Pichia anomala* NBRC 0120 | 40 | 90/10 | 63 | (2S,3S) | 6 | (2S,3R) |
| *Pichia angusta* IAM 12898 | 24 | 98/2 | 62 | (2R,3R) | | |
| *Pichia haplophila* NBRC 0947 | 25 | 84/16 | 57 | (2S,3S) | 82 | (2S,3R) |
| *Pichia holstii* NBRC 0980 | 30 | 98/2 | 58 | (2R,3R) | | |
| *Pichia jadinii* NBRC 0987 | 27 | 95/5 | 73 | (2R,3R) | >99 | (2S,3R) |
| *Pichia pastoris* NBRC 0948 | 45 | 97/3 | 84 | (2R,3R) | >99 | (2S,3R) |
| *Pichia petersonii* NBRC 1372 | 11 | 90/10 | 74 | (2R,3R) | 31 | (2S,3R) |
| *Pichia rhodanensis* NBRC 1272 | 27 | 93/7 | 57 | (2R,3R) | 36 | (2S,3R) |
| *Pichia wickerhamii* NBRC 1706 | 26 | 95/5 | 79 | (2R,3R) | >99 | (2S,3R) |
| *Pichia membranifaciens* NBRC 0128 | 44 | 100/0 | 74 | (2R,3R) | | |
| *Pichia xylosa* NBRC 0950 | 15 | 99/1 | 74 | (2R,3R) | | |
| *Rhodotorula minuta* NBRC 0387 | 19 | 98/2 | 78 | (2R,3R) | | |
| *Saccharomyces unisporus* NBRC 0215 | 58 | 100/0 | 77 | (2R,3R) | | |
| *Saccharomyces bayanus* NBRC 0213 | 23 | 92/8 | 75 | (2R,3R) | >99 | (2R,3S) |
| *Saccharomyces cerevisiae hansen* HUT 7017 | 29 | 90/10 | 75 | (2R,3R) | 80 | (2R,3S) |
| *Saccharomyces cerevisiae* var. *ellipsoideus* HUT 7135 | 32 | 98/2 | 77 | (2R,3R) | 55 | (2R,3S) |
| *Saccharomyces uvarum* OUT 7931 | 38 | 100/0 | 80 | (2R,3R) | | |
| *Saccharomyces pastorianus* NBRC 1265 | 23 | 96/4 | 78 | (2R,3R) | >99 | (2R,3S) |
| *Saccharomycodes ludwigii* NBRC 0798 | 23 | 100/0 | 87 | (2R,3R) | | |
| *Saccharomycopsis crataegensis* NBRC 1708 | 24 | 93/7 | 68 | (2R,3R) | 42 | (2R,3S) |
| *Saccharomycopsis malanga* NBRC 1710 | 55 | 67/33 | 68 | (2S,3S) | 77 | (2R,3S) |
| *Saccharomycopsis javanensis* NBRC 1848 | 30 | 94/6 | 90 | (2R,3R) | 10 | (2S,3R) |
| *Schizosaccharomyces pombe* NBRC 0347 | 37 | 97/3 | 89 | (2R,3R) | 36 | (2R,3S) |
| *Saturnispora dispora* NBRC 0035 | 45 | 100/0 | 96 | (2R,3R) | | |
| *Torulaspora globosa* NBRC 0016 | 54 | 95/5 | 63 | (2R,3R) | 80 | (2R,3S) |
| *Williopsis satumus* var. *suaveolens* NBRC 0809 | 17 | 69/31 | 67 | (2S,3S) | 58 | (2S,3R) |
| *Williopsis satumus* var. *satumus* NBRC 0992 | 24 | 87/13 | 58 | (2R,3R) | 53 | (2S,3R) |
| *Zygosaccharomyces beilii* NBRC 0488 | 47 | 95/5 | 78 | (2R,3R) | 39 | (2R,3S) |
| *Zygosaccharomyces rouxii* NBRC 0686 | 57 | 98/2 | 79 | (2R,3R) | 1 | (2R,3S) |

Example 17

Reduction of ethyl 2-chloro-3-oxohexanoate with bacteria

A liquid medium (pH 7.0) containing 1% of broth, 1% of polypeptone, 0.5% of yeast extract and 0.3% of NaCl was prepared; and the liquid medium was put into large-size test tubes in an amount of 5 ml each, and was sterilized with steam at 120° C. for 20 minutes. One platinum loop of bacteria shown in Table 3 were inoculated into the liquid medium, and were incubated with shaking at 30° C. for 2 to 3 days. The cells were collected from the liquid medium by centrifugation or suction filtration, washed with water, and suspended in 0.1 M phosphate buffer (pH 5.5, 0.5 ml). Using the cell suspension, the reaction and the extraction were carried out under the same condition as in Example 16, and the yield (%), the diastereomer ratio (anti/syn) and the optical purity (% e.e.) were determined. The results are shown in Table 3.

TABLE 3

| Microorganisms | Yield (%) | Anti/Syn | Anti Form Optical purity (% e.e.) | Configuration | Syn Form Optical purity (% e.e.) | Configuration |
|---|---|---|---|---|---|---|
| *Achromobacter xylosoxidans* subsp. *denitrificans* NBRC 15125 | 17 | 96/4 | 95 | (2S,3S) | 23 | (2S,3R) |
| *Arthrobacter crystallopoietes* NBRC 14235 | 8 | 94/6 | 94 | (2S,3S) | 77 | (2R,3S) |
| *Arthrobacter nicotianae* NBRC 14234 | 8 | 96/4 | 89 | (2S,3S) | >99 | (2R,3S) |
| *Arthrobacter protophormiae* NBRC 12128 | 7 | 97/3 | 93 | (2S,3S) | | |
| *Acidiphilium cryptum* NBRC 14242 | 24 | 99/1 | 95 | (2S,3S) | 22 | (2R,3S) |
| *Cellulomonas fermentans* NBRC 15517 | 9 | 97/3 | 92 | (2S,3S) | | |
| *Corynebacterium flavescens* NBRC 14136 | 73 | 96/4 | 80 | (2R,3R) | 80 | (2S,3R) |
| *Corynebacterium glutamicum* ATCC 21269 | 6 | 91/9 | 72 | (2R,3R) | 13 | (2S,3R) |
| *Microbacterium arborescens* NBRC 3750 | 26 | 100/0 | 95 | (2S,3S) | | |
| *Micrococcus luteus* NBRC 13867 | 7 | 100/0 | 93 | (2S,3S) | | |
| *Ochrobactrum* sp. NBRC 12950 | 27 | 65/35 | 97 | (2S,3S) | >99 | (2R,3S) |
| *Oerskovia turbata* NBRC 15015 | 20 | 94/6 | 86 | (2S,3S) | 70 | (2R,3S) |
| *Pseudomonas stutzeri* NBRC 13596 | 9 | 95/5 | 88 | (2S,3S) | 42 | (2R,3S) |
| *Pseudomonas putida* NBRC 14164 | 69 | 100/0 | 98 | (2S,3S) | | |
| *Paenibacillus alvei* NBRC 3343 | 6 | 97/3 | 79 | (2S,3S) | | |

Example 18

Reduction of ethyl 2-chloro-3-oxohexanoate with actinomycete

The yield (%), the diastereomer ratio (anti/syn) and the optical purity (% e.e.) in the case of using the microorganisms shown in Table 4 were determined by the same process as in Example 17 except that a liquid medium (pH 7.2) containing 3% of tryptic soy broth and 1% of soluble starch was used. The results are shown in Table 4.

TABLE 4

| Microorganisms | Yield (%) | Anti/Syn | Anti Form Optical purity (% e.e.) | Anti Form Configuration | Syn Form Optical purity (% e.e.) | Syn Form Configuration |
|---|---|---|---|---|---|---|
| Streptomyces aureus NIHJ 122 | 22 | 95/5 | 81 | (2S,3S) | 27 | (2R,3S) |
| Streptomyces cacaoi subsp. asoensis NBRC 13813 | 89 | 100/0 | 97 | (2S,3S) | | |
| Streptomyces coelescens NBRC 13378 | 6 | 87/13 | 80 | (2S,3S) | 60 | (2R,3S) |
| Streptomyces griseoaurantiacus NBRC 15440 | 6 | 100/0 | 96 | (2S,3S) | | |
| Streptomyces hydrogenans NBRC 13475 | 31 | 96/4 | 83 | (2S,3S) | 7 | (2S,3R) |
| Streptomyces salmonis NBRC 15865 | 6 | 94/6 | 91 | (2S,3S) | | |
| Saccharopolyspora erythraea NBRC 13426 | 14 | 91/9 | 58 | (2S,3S) | 23 | (2S,3R) |

Example 19

Reduction of ethyl 2-chloro-3-oxohexanoate with mold

The yield (%), the diastereomer ratio (anti/syn) and the optical purity (% e.e.) in the case of using the mold shown in Table 5 were determined by the same process as in Example 16 except that a liquid medium (pH 7.0) containing 1% of broth, 1% of polypeptone, 1% of glucose, 0.5% of yeast extract, 0.1% of NaCl and 0.05% of $MgSO_4 \cdot 7H_2O$ was used. The results are shown in Table 5.

TABLE 5

| Microorganisms | Yield (%) | Anti/Syn | Anti Form Optical purity (% e.e.) | Anti Form Configuration | Syn Form Optical purity (% e.e.) | Syn Form Configuration |
|---|---|---|---|---|---|---|
| Aegerita candida NBRC 6988 | 9 | 86/14 | 72 | (2S,3S) | >99 | (2R,3S) |
| Cladosporium resinae NBRC 8588 | 18 | 100/0 | 96 | (2R,3R) | | |
| Cordyceps subsessilis AMA 5183 | 49 | 100/0 | 97 | (2R,3R) | | |
| Cariolus consors NBRC 9078 | 11 | 80/20 | 86 | (2R,3R) | 33 | (2S,3R) |
| Dendryphiella salina NBRC 8281 | 8 | 80/20 | 73 | (2R,3R) | 60 | (2S,3R) |
| Emericella nidulans var. nidulans NBRC 4340 | 6 | 100/0 | 97 | (2R,3R) | | |
| Emericella unguis NBRC 8087 | 13 | 100/0 | 96 | (2R,3R) | | |
| Fusarium anguioides NBRC 4467 | 10 | 78/22 | 52 | (2R,3R) | >99 | (2S,3R) |
| Gloeophyllum trabeum NBRC 6430 | 16 | 99/1 | 93 | (2R,3R) | >99 | (2S,3R) |
| Lentinula edodes NBRC 8340 | 6 | 100/0 | 90 | (2R,3R) | | |
| Macrophoma commelinae NBRC 9569 | 7 | 100/0 | 83 | (2R,3R) | | |
| Monascus purpureus NBRC 5965 | 30 | 93/7 | 66 | (2R,3R) | 40 | (2R,3S) |
| Myrothecium verrucaria IAM 5063 | 34 | 99/1 | 94 | (2R,3R) | 6 | (2S,3R) |
| Nannizzia gypsea var. incurvata NBRC 8306 | 30 | 100/0 | 95 | (2R,3R) | | |
| Panus lacomtei NBRC 31653 | 19 | 99/1 | 72 | (2R,3R) | 21 | (2R,3S) |
| Penicillium janthinellum NBRC 4651 | 6 | 88/12 | 76 | (2R,3R) | >99 | (2S,3R) |
| Plectosphaerella cucumerina NBRC 30005 | 39 | 85/15 | 69 | (2R,3R) | 72 | (2S,3R) |
| Pycnoporus coccineus NBRC 9768 | 10 | 83/17 | 50 | (2R,3R) | 28 | (2R,3S) |
| Phanerochaete chrysosporium NBRC 31249 | 23 | 93/7 | 75 | (2R,3R) | 35 | (2R,3S) |
| Rhizopus niveus NBRC 4759 | 27 | 91/9 | 92 | (2R,3R) | >99 | (2S,3R) |
| Rhizopus oryzae NBRC 4705 | 20 | 90/10 | 90 | (2R,3R) | >99 | (2S,3R) |
| Rhizopus stolonifer var. stolonifer NBRC 4781 | 19 | 86/14 | 90 | (2R,3R) | >99 | (2S,3R) |
| Scopulariopsis brevicaulis NBRC 4843 | 18 | 98/2 | 93 | (2R,3R) | >99 | (2S,3R) |

TABLE 5-continued

| Microorganisms | Yield (%) | Anti/Syn | Anti Form | | Syn Form | |
| --- | --- | --- | --- | --- | --- | --- |
| | | | Optical purity (% e.e.) | Configuration | Optical purity (% e.e.) | Configuration |
| *Sporotrichum aurantiacum* NBRC 9381 | 12 | 89/11 | 56 | (2R,3R) | 46 | (2R,3S) |
| *Umbelopsis vinacea* NBRC 6738 | 28 | 79/21 | 82 | (2R,3R) | 90 | (2S,3R) |
| *Verticillium niveostratosum* NBRC 5435 | 21 | 100/0 | 98 | (2R,3R) | | |

Example 20

Reduction of ethyl 2-chloro-3-oxohexanoate with recombinant *Escherichia coli*

A medium (50 ml) containing 1.6% of bacto-tryptone, 1% of bacto-yeast extract and 0.5% of NaCl (pH 7.0) was put into a 500-ml Sakaguchi flask and the medium was sterilized. Then, *Escherichia coli* HB101 (pTSCS) of which acceptance number is FERM BP-10024 was inculcated therein, and was incubated with shaking at 37° C. for 24 hours. To the obtained culture broth (50 ml), ethyl 2-chloro-3-oxohexanoate (1 g), glucose dehydrogenase manufactured by Amano Enzyme (100 units), glucose (1280 mg) and oxidized nicotinamide adenine dinucleotide (NAD+, 2.5 mg) were added. The reaction was carried out for 24 hours with keeping the pH at 6.5 with 30% NaOH. After the reaction, the mixture was extracted twice with 100 ml of ethyl acetate, and the obtained organic layer was concentrated under reduced pressure to obtain oily ethyl 2-chloro-3-hydroxyhexanoate (0.96 g). The obtained product was analyzed by GC. As a result, anti/syn=99/1 and the optical purity of the anti-form (2S,3S) was 99.7% e.e.

Example 21

Production of ethyl (3R)-2-chloro-3-hydroxy-4-phenylbutyrate

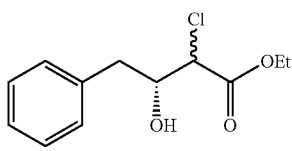

Ethyl 2-chloro-3-oxo-4-phenylbutyrate (180 mg, 0.7 mmol) and RuCl[(S,S)-TsDPEN]$_p$-cymene) complex (10 mg, 2 mol %) were mixed, and the mixture was dissolved in chlorobenzene (1 ml). A chlorobenzene solution (1 ml) of triethylamine (374 mg, 5 equivalents) was added, and then a chlorobenzene solution (1 ml) of formic acid (102 mg, 3 equivalents) was gradually added dropwise. After the mixture was stirred at 40° C. for 3 hours, water (4 ml) was added. Ethyl acetate (10 ml) was added for extraction, and the organic layer was concentrated under reduced pressure to obtain the title compound as a brown oil (182 mg, yield: 100%).

$^1$H NMR (400 MHz, CDCl$_3$): δ 7.41-7.22 (m, 5H), 4.23 (q, 2H), 4.15 (d, 1H), 3.11 (dd, 1H), 2.90 (dd, 1H), 2.5 (brs, 1H), 1.29 (t, 3H)

Example 22

Production of (2S,3R)-3-benzyl-2-oxiranecarboxylic acid

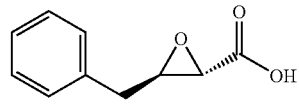

Ethyl (3R)-2-chloro-3-hydroxy-4-phenylbutyrate (122 mg, 0.5 mmol) was dissolved in ethanol (3 ml), and 20 wt % sodium ethoxide/ethanol solution (254 mg) was gradually added. The mixture was stirred at room temperature for 3 hours, and the solvent was evaporated away under reduced pressure. Water (5 ml) was added, and the pH was adjusted to 13 with 30 wt % aqueous solution of sodium hydroxide. The mixture was washed with toluene (5 ml), and the pH was adjusted to 1.5 with concentrated hydrochloric acid. The mixture was extracted with ethyl acetate (15 ml), and drying was carried out with anhydrous magnesium sulfate. The solvent was evaporated away under reduced pressure to obtain the title compound as a brown oil (66 mg, yield: 74%).

$^1$H NMR (400 MHz, CDCl$_3$): δ 9.33 (brs, 1H), 7.43-7.18 (m, 5H), 3.40 (dt, 1H), 3.30 (s, 1H)

Example 23

Production of (2S,3R)-3-benzyl-2-oxiranecarboxylic cyclopropylamide

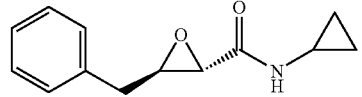

(2S,3R)-3-Benzyl-2-oxiranecarboxylic acid (66 mg) and a chlorobenzene solution (2 ml) of cyclopropylamine (23.2 mg, 1.1 equivalents) were mixed, and the mixture was cooled to 5° C. A methylene chloride solution (2 ml) of 1-ethyl-3-(3-dimethylaminopropyl)carbodiimide hydrochloride (1.5 equivalents) was gradually added, and the mixture was stirred at room temperature for 14 hours. Saturated aqueous solution of sodium hydrogencarbonate (5 ml) was added to the reaction mixture, and the reaction mixture was extracted with ethyl acetate (10 ml). The organic layer was washed with 1 N hydrochloric acid (5 ml) and water (5 ml) in order, and the solvent was evaporated away under reduced pressure to obtain the title compound as a brown oil (50 mg, yield: 62%).

¹H NMR (400 MHz, CDCl₃): δ 7.30-7.15 (m, 5H), 6.23 (brs, 1H), 3.28 (d, 1H), 3.14 (ddd, 1H), 3.05 (dd, 1H), 2.80 (dd, 1H), 0.75 (dt, 2H), 0.47 (dt, 2H)

Example 24

Production of (4S,5S)—N-cyclopropyl-2-isopropyl-4-benzyl-4,5-dihydro-1,3-oxazole-5-carboxamide

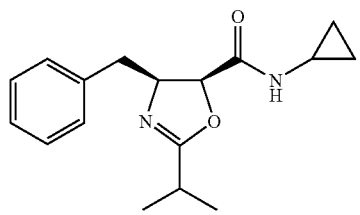

(2S,3R)-3-Benzyl-2-oxiranecarboxylic cyclopropylamide (50 mg) and isobutyronitrile (2 ml) were mixed, and the mixture was cooled to 5° C. Boron trifluoride diethyl ether complex (2.5 equivalents) was gradually added, and the mixture was stirred at 5 to 20° C. for 2 hours. A mixture solution of ethyl acetate (10 ml) and saturated aqueous solution of sodium hydrogencarbonate (5 ml) was kept cooled at 5° C., and the reaction mixture was gradually added thereinto dropwise. The aqueous layer was removed, and then the solvent was evaporated away under reduced pressure to obtain the title compound as a brown solid (63 mg, yield: 96%).

¹H NMR (400 MHz, CDCl₃): δ 7.30-7.18 (m, 5H), 6.25 (brs, 1H), 4.84 (d, 1H), 4.60 (dt, 1H), 3.16 (dd, 1H), 2.76 (tt, 1H), 2.60 (dd, 1H), 2.52 (dd, 1H), 1.20 (d, 6H), 0.83 (dd, 2H), 0.57 (dd, 2H)

Example 25

Production of (2S,3S)-2-hydroxy-3-amino-4-phenylbutyric acid hydrochloride

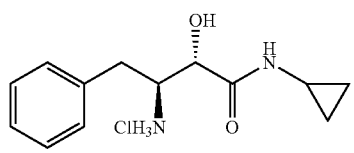

(4S,5S)—N-Cyclopropyl-2-isopropyl-4-benzyl-4,5-dihydro-1,3-oxazole-5-carboxamide (63 mg), acetone (2.5 ml) and concentrated hydrochloric acid (0.25 g) were mixed, and the mixture was stirred at 50° C. for 23 hours. The reaction mixture was concentrated, and isopropanol (5 ml) was added. The mixture was concentrated under reduced pressure. The same operation was further repeated, and then isopropanol (3 ml) was added to precipitate a crystal. The crystal was collected by filtration under reduced pressure, and was dried in vacuum to obtain the title compound as a white crystal (23 mg, yield: 36%).

¹H NMR (400 MHz, D₂O): δ 7.27-7.16 (m, 5H), 4.27 (brs, 1H), 3.98-3.80 (m, 1H), 2.95-2.85 (m, 1H), 2.26-2.22 (m, 1H), 0.83 (dd, 2H), 0.57 (dd, 2H)

Example 26

Production of ethyl (2S,3R)-2-chloro-3-hydroxyhexanoate

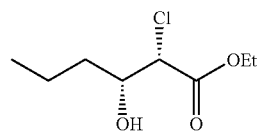

Ethyl 2-chloro-3-oxohexanoate (194 mg), DMF (2.4 ml), RuCl[(S,S)-MesDPEN](p-cymene) complex (1 mol %) and triethylamine (5 equivalents) were mixed, and formic acid (5 equivalents) was gradually added thereto. The reaction was carried out at 40° C. for 3 hours. The reaction mixture was analyzed. As a result, the conversion ratio was 97%, and the isomer ratio of (2S,3R):(2S,3S):(2R,3R):(2R,3S) is 94.7:1.3:0:4.0. In the above, "Mes" represents a methylenesulfonyl group.

Example 27

Production of ethyl (2S,3R)-2-chloro-3-hydroxyhexanoate

Ethyl 2-chloro-3-oxohexanoate (194 mg), DMF (2.4 ml), RuCl[(S,S)—NpDPEN](p-cymene) complex (1 mol %) and triethylamine (5 equivalents) were mixed, and formic acid (5 equivalents) was gradually added thereto. The reaction was carried out at 40° C. for 3 hours. The reaction mixture was analyzed. As a result, the conversion ratio was 95%, and the isomer ratio of (2S,3R):(2S,3S):(2R,3R):(2R,3S) is 88.3:4.6:2.1:5.1.

Example 28

Production of ethyl 2-chloro-3-hydroxyhexanoate

Ethyl 2-chloro-3-oxohexanoate (194 mg), chlorobenzene (3 ml), RuCl[(S,S)-TsDPEN](p-cymene) complex (1 mol %) and triethylamine (5 equivalents) were mixed, and formic acid (3 equivalents) was gradually added thereto. The reaction was carried out at 40° C. for 3 hours. The reaction mixture was analyzed. As a result, the conversion ratio was 100%, and the isomer ratio of (2S,3R):(2S,3S):(2R,3R):(2R,3S) is 63.7:24.9:4.1:7.3.

Reference Example 1

Production of ethyl 3-oxo-4-phenylbutyrate

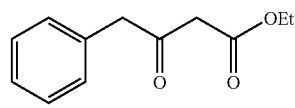

Monoethyl monopotassium malonate (12.9 g, 2.3 equivalents) was mixed with tetrahydrofuran (200 ml), and the mixture was cooled to 5° C. Triethylamine (8.2 g, 2.5 equivalents) and magnesium chloride (8.62 g, 2.8 equivalents) were added, and the mixture was stirred at 5 to 20° C. for 3 hours. The reaction mixture was cooled to 5° C. Phenacyl chloride (5 g, 32 mmol, 1 equivalent) was gradually added, and the mixture was stirred at 5 to 20° C. for 63 hours. The mixture was cooled to 5° C., and 1 N hydrochloric acid (30 ml) was added. Tetrahydrofuran was evaporated away under reduced pressure, and extraction was carried out with ethyl acetate (50 ml). The organic layer was washed with 1 N hydrochloric acid (30 ml), water (10 ml), saturated aqueous solution of sodium hydrogencarbonate (30 ml) and water (10 ml) in order. The solvent was evaporated away under reduced pressure to obtain the title compound as a pale yellow oil (5.82 g, yield: 86%).

Reference Example 2

Production of ethyl 2-chloro-3-oxo-4-phenylbutyrate

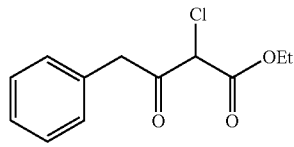

Ethyl 3-oxo-4-phenylbutyrate (4.8 g, 23 mmol) and methylene chloride (48 ml) were mixed, and sulfuryl chloride (3.1 g, 1 equivalent) was gradually added thereto dropwise. After the addition, the mixture was stirred at 20° C. for 1 hour. The reaction mixture was concentrated under reduced pressure, and saturated aqueous solution of sodium hydrogencarbonate (10 ml) was added, and extraction was carried out with ethyl acetate (20 ml). The solvent was evaporated away under reduced pressure and drying was carried out in vacuum to obtain the title compound as a yellow oil (4.8 g, yield: 86%).

Example 29

Production of (4S,5S)—N-cyclopropyl-2-isopropyl-4-propyl-4,5-dihydro-1,3-oxazole-5-carboxamide

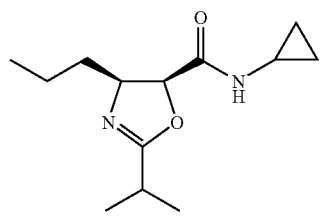

Isobutyronitrile (6.8 g) was added to ethyl (2S,3R)-3-propyl-2-oxiranecarboxylate (3.2 g, 19 mmol), and the mixture was cooled to 5° C. Boron trifluoride diethyl ether complex (5.5 g, 2 equivalents) was gradually added dropwise, and the mixture was stirred at room temperature for 2 hours. Ethyl acetate (40 ml) and saturated aqueous solution of sodium hydrogencarbonate (13 ml) were mixed, and the mixture was kept cooled at 5° C. The reaction mixture was added thereto. The pH was adjusted at 6.7, and the aqueous layer was removed. The organic layer was washed with saturated aqueous solution of sodium chloride (8 ml), and the solvent was evaporated away under reduced pressure to obtain the title compound as a yellow solid (6.23 g, yield: 90%).

$^1$H NMR (400 MHz, CDCl$_3$): δ 6.24 (brs, 1H), 4.80 (d, 1H), 4.36 (dt, 1H), 2.80-2.55 (m, 2H), 1.80-1.36 (m, 3H), 1.22-1.05 (m, 7H), 0.95 (t, 3H), 0.83-0.80 (m, 2H), 0.55-0.50 (m, 2H)

Example 30

Production of (2S,3S)-3-amino-2-hydroxy-hexanoic cyclopropylamide hydrochloride (4S,5S)—N-Cyclopropyl-2-isopropyl-4-propyl-4,5-dihydro-1,3-oxazole-5-carboxamide (3.11 g, 8.7 mmol), acetone (15 ml) and concentrated hydrochloric acid (1.39 g, 1.5 equivalents) were mixed, and the mixture was stirred at 50° C. for 39 hours. The solvent was evaporated away under reduced pressure. Isopropanol (10 ml) was added, and the mixture was concentrated. The same operation was repeated again. Methanol (2.7 ml) was added to the obtained solid, and the mixture was stirred at 60° C. for 1 hour. Ethyl acetate (20 ml) was gradually added thereto dropwise. After the addition, the mixture was gradually cooled to 5° C. The precipitated crystal was collected by filtration, and dried under reduced pressure to obtain the title compound as a white crystal (1.36 g, yield: 72%).

Example 31

Reduction of ethyl 2-chloro-3-oxo-4-phenylbutyrate with recombinant *Escherichia coli*

A medium (50 ml) containing 1.6% of bacto-tryptone, 1% of bacto-yeast extract and 0.5% of NaCl (pH 7.0) was put into a 500 ml Sakaguchi flask, and was sterilized. Then, *Escherichia coli* HB101 (pNTRDG1) of which acceptance number is FERM BP-08458 was inculcated therein, and was incubated with shaking at 37° C. for 24 hours. Ethyl 2-chloro-3-oxo-4-phenylbutyrate (1 g), glucose (2 g) and oxidized nicotinamide adenine dinucleotide (NAD$^+$, 2.5 mg) were added to the obtained culture broth (50 ml), and reaction was carried out for 24 hours with keeping the pH at 6.5 with 30% NaOH. After the reaction, extraction was carried out twice with 100 ml of ethyl acetate, and the obtained organic layer was concentrated under reduced pressure to obtain oily ethyl 2-chloro-3-hydroxy-4-phenylbutyrate (0.96 g). The obtained product was analyzed by GC. As a result, anti/syn=99/1 and the optical purity of the anti-form (2S,3S) was 99.8% e.e.

The invention claimed is:
1. An optically-active oxazolinamide derivative represented by the following formula (1):

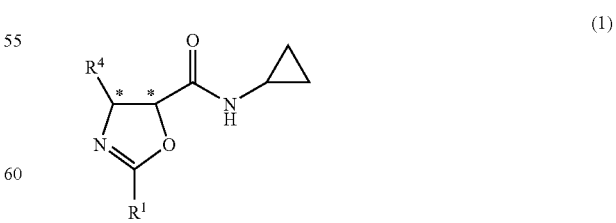

(1)

wherein, * indicates an asymmetric carbon atom; R$^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent.

2. An optically-active oxazoline carboxylic acid derivative represented by the following formula (5):

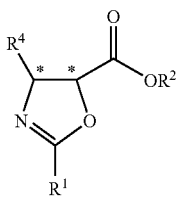

(5)

wherein, * indicates an asymmetric carbon atom; $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent.

3. A compound represented by the following formula (17):

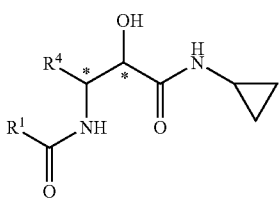

(17)

wherein, * indicates an asymmetric carbon atom; $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent.

4. A method for producing an optically-active 2-halo-3-hydroxypropionic acid derivative;

comprising a step of asymmetric reduction of a 2-halo-3-oxopropionic acid derivative represented by the following formula (10):

(10)

wherein, $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; X represents a halogen atom; $R^4$ represents an alkyl group having 1 to 20 carbon atoms and optionally having a substituent, or an aralkyl group having 7 to 20 carbon atoms and optionally having a substituent;

wherein the optically-active 2-halo-3-hydroxypropionic acid derivative is represented by the following formula (11):

(11)

wherein, * indicates an asymmetric carbon atom; $R^2$, $R^4$ and X are the same as above.

5. A method for producing an optically-active epoxyamide derivative;

comprising a step of reacting an optically-active epoxycarboxylic acid derivative represented by the following formula (7):

(7)

wherein, * indicates an asymmetric carbon atom; $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent with a cyclopropylamine represented by the following formula (6):

(6)

wherein, the optically-active epoxyamide derivative is represented by the following formula (3):

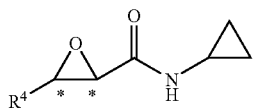
(3)

wherein, * is the same as above; $R^4$ represents an alkyl group having 1 to 20 carbon atoms and optionally having a substituent, or an aralkyl group having 7 to 20 carbon atoms and optionally having a substituent.

6. The method for producing the optically-active epoxyamide derivative according to claim 5; wherein
the compound (7) wherein $R^2$ is a hydrogen atom is reacted with an alkoxycarbonyl chloride, a dialkyl dicarbonate or pivaloyl chloride in a presence of a base to obtain a mixed acid anhydride; and
the mixed acid anhydride is reacted with the cyclopropylamine of the formula (6).

7. A method for producing an optically-active oxazolinamide derivative;
comprising a step of reacting an optically-active epoxyamide derivative represented by the following formula (3):

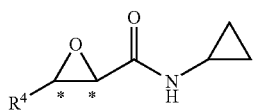
(3)

wherein, * indicates an asymmetric carbon atom; $R^4$ represents an alkyl group having 1 to 20 carbon atoms and optionally having a substituent, or an aralkyl group having 7 to 20 carbon atoms and optionally having a substituent
with a nitrile represented by the following formula (4):

$R^1CN$ (4)

wherein, $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent in a presence of an acid catalyst; and
wherein the optically-active oxazolinamide derivative is represented by the following formula (1):

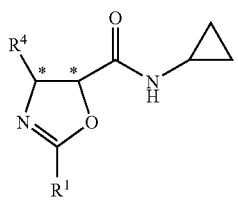
(1)

wherein, *, $R^1$ and $R^4$ are the same as above.

8. The method for producing the optically-active oxazolinamide derivative according to claim 7, wherein the compound (3) is obtained by a method comprising a step of reacting an optically-active epoxycarboxylic acid derivative represented by the following formula (7):

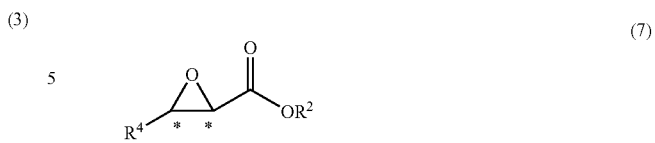
(7)

wherein, * and $R^4$ are the same as above; $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent
with a cyclopropylamine represented by the following formula (6):

(6)

9. A method for producing an optically-active oxazolinamide derivative;

comprising steps of reacting an optically-active epoxycarboxylic acid derivative represented by the following formula (7):

(7)

wherein, * indicates an asymmetric carbon atom; $R^2$ represents a hydrogen atom, an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent
with a nitrile represented by the following formula (4):

$R^1CN$ (4)

wherein $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent
in a presence of an acid catalyst to produce an optically-active oxazolinecarboxylic acid derivative represented by the following formula (5):

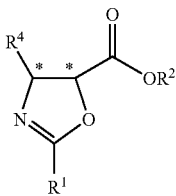

wherein, *, $R^1$, $R^2$ and $R^4$ are the same as above; and
then reacting the optically-active oxazolinecarboxylic acid derivative with a cyclopropylamine represented by the following formula (6):

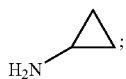

wherein the optically-active oxazolinamide derivative is represented by the following formula (1):

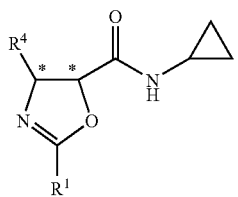

wherein, *, $R^1$ and $R^4$ are the same as above.

10. A method for producing an optically-active 3-amino-2-hydroxypropionic cyclopropylamide derivative or salt thereof;
comprising a step of selective acid hydrolysis or acid alcoholysis of an oxazoline ring of an optically-active oxazolinamide derivative represented by the following formula (1):

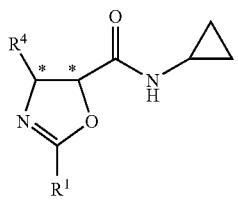

wherein, * indicates an asymmetric carbon atom; $R^1$ represents an alkyl group having 1 to 20 carbon atoms and optionally having a substituent, an alkenyl group having 2 to 20 carbon atoms and optionally having a substituent, an aryl group having 6 to 20 carbon atoms and optionally having a substituent, or an aralkyl group having 7 to 20 carbon atoms and optionally having a substituent; $R^4$ represents an alkyl group having 1 to 20 carbon atoms and optionally having a substituent, or an aralkyl group having 7 to 20 carbon atoms and optionally having a substituent;

wherein the optically-active 3-amino-2-hydroxypropionic cyclopropylamide derivative is represented by the following formula (2):

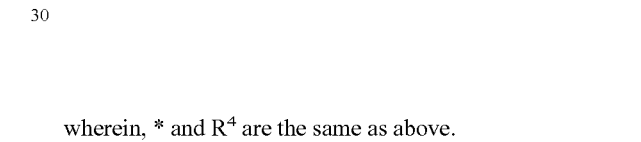

wherein, * and $R^4$ are the same as above.

11. The optically-active oxazolinamide derivative according to claim 1, wherein $R^4$ is an n-propyl group.

12. The optically-active oxazoline carboxylic acid derivative according to claim 2, wherein $R^4$ is an n-propyl group.

13. The compound according to claim 3, wherein $R^4$ is an n-propyl group.

14. The method according to claim 4, wherein $R^4$ is an n-propyl group.

15. The method according to claim 5, wherein $R^4$ is an n-propyl group.

16. The method according to claim 7, wherein $R^4$ is an n-propyl group.

17. The method according to claim 9, wherein $R^4$ is an n-propyl group.

18. The method according to claim 10, wherein $R^4$ is an n-propyl group.

* * * * *